United States Patent
Inge

(10) Patent No.: US 10,684,290 B2
(45) Date of Patent: Jun. 16, 2020

(54) LKB1 RELATED DIAGNOSTICS AND TREATMENTS OF CANCER

(71) Applicant: Dignity Health, Phoenix, AZ (US)

(72) Inventor: Landon J. Inge, Phoenix, AZ (US)

(73) Assignee: Dignity Health, Phoenix, AZ (US)

( * ) Notice: Subject to any disclaimer, the term of this patent is extended or adjusted under 35 U.S.C. 154(b) by 563 days.

(21) Appl. No.: 15/112,090

(22) PCT Filed: Feb. 18, 2015

(86) PCT No.: PCT/US2015/016304
§ 371 (c)(1),
(2) Date: Jul. 15, 2016

(87) PCT Pub. No.: WO2015/126898
PCT Pub. Date: Aug. 27, 2015

(65) Prior Publication Data
US 2016/0356787 A1   Dec. 8, 2016

Related U.S. Application Data

(60) Provisional application No. 61/941,375, filed on Feb. 18, 2014.

(51) Int. Cl.
| | |
|---|---|
| *G01N 31/00* | (2006.01) |
| *G01N 33/53* | (2006.01) |
| *G01N 33/68* | (2006.01) |
| *A61K 31/635* | (2006.01) |
| *A61K 31/7004* | (2006.01) |
| *A61K 31/166* | (2006.01) |
| *G01N 33/574* | (2006.01) |
| *A61K 31/365* | (2006.01) |
| *A61K 31/395* | (2006.01) |
| *A61K 31/472* | (2006.01) |
| *A61K 31/519* | (2006.01) |
| *A61K 31/63* | (2006.01) |
| *A61K 31/69* | (2006.01) |
| *A61K 31/7072* | (2006.01) |
| *A61K 31/7076* | (2006.01) |
| *C12Q 1/48* | (2006.01) |

(52) U.S. Cl.
CPC ....... *G01N 33/6863* (2013.01); *A61K 31/166* (2013.01); *A61K 31/365* (2013.01); *A61K 31/395* (2013.01); *A61K 31/472* (2013.01); *A61K 31/519* (2013.01); *A61K 31/63* (2013.01); *A61K 31/635* (2013.01); *A61K 31/69* (2013.01); *A61K 31/7004* (2013.01); *A61K 31/7072* (2013.01); *A61K 31/7076* (2013.01); *C12Q 1/485* (2013.01); *G01N 33/57423* (2013.01); *G01N 2333/521* (2013.01); *G01N 2333/523* (2013.01); *G01N 2333/912* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2011/0145176 A1* | 6/2011 | Perou | ........... C12Q 1/6886 706/12 |
| 2012/0122991 A1 | 5/2012 | Cantley et al. | |
| 2013/0072485 A1 | 3/2013 | Gray et al. | |
| 2013/0338040 A1 | 12/2013 | Hayes et al. | |

FOREIGN PATENT DOCUMENTS

| | | |
|---|---|---|
| CA | 2934626 A1 | 8/2015 |
| EP | 1888114 B1 | 9/2013 |
| EP | 3108013 A1 | 12/2016 |
| WO | 2008097908 A2 | 8/2008 |
| WO | 2011085163 A2 | 7/2011 |
| WO | 2015126898 A1 | 8/2015 |

OTHER PUBLICATIONS

Shackelford et al. (Cancer Cell, Feb. 11, 2013; vol. 23, No. 2, pp. 143-158).*
Shackelford et al. Supplemental Data (Cancer Feb. 11, 2013; vol. 23, No. 2, pp. 143-158).*
Saito et al. (Cancer Research, 2009; vol. 69, No. 10, May 15, 2009).*
Shackelford (Cancer Cell 23(2): 142-158 and Supplemental Information, pp. 1-19, Feb. 11, 2013).*
Saito et al. (Cancer Research 69(10): 4225-34, 2009).*
Ferreira et al. (Journal of Clinical Oncology, 30(15), Jan. 2, 2012, Tumor Biology, Abstract e21073).*
Massey (J. Med Chem. 2010, vol. 53, pp. 7280-7286).*
PCT/US2015/016304 International Search Report and Written Opinion dated Jul. 6, 2015; 11 pages.
Cai et al. Monocyte Chemotactic Protein 1 Promotes Lung Cancer-Induced Bone Resorptive Lesions In Vivo. Neoplasia (2009). 11(3)228-236.
Gills et al. Nelfinavir, A Lead HIV Protease Inhibitor, is a Broad-Spectrum, Anticancer Agent that Induces Endoplasmic Reticulum Stress, Autophagy, and Apoptosis In vitro and In vivo. Clin Cancer Res (2007). 13:5183-5194.
Hung et al. Prognostic significance of hypoxia-inducible factor-1a, TWIST1 and Snail expression in resectable non-small cell lung cancer. Thorax (2009). 64(12):1082-1089.

(Continued)

*Primary Examiner* — Lisa V Cook
(74) *Attorney, Agent, or Firm* — Rodney J. Fuller; Booth Udall Fuller, PLC

(57) ABSTRACT

Described herein are methods and compositions for the diagnosis, prognosis, selection of treatment and treatment of cancer, and particularly, of lung cancer such as non-small cell lung cancer. Embodiments of the present invention involve the detection of LKB1 levels and sensitivity to endoplasmic reticulum (ER) stress. Treatment can be made through the administration of ER stress activators.

7 Claims, 17 Drawing Sheets

Specification includes a Sequence Listing.

(56) References Cited

OTHER PUBLICATIONS

Ferreira, Ana Carolina et al., "Association of serum CCL2 with advanced stage, metastasis, and smoking history in non-small cell lung cancer patients", Journal of Clinical Oncology, 30(15), (Jan. 1, 2012).

Sher, Yuh-Pyng et al., "Prognosis of Non-Small Cell Lung Cancer Patients by Detecting Circulating Cancer Cells in the Peripheral Blood with Multiple Marker Genes", Clinical Cancer Research, 11:173-179 (Jan. 1, 2005).

Swinson, Daniel Edmund Bryan et al., "Interactions between hypoxia and epidermal growth factor receptor in non-small-cell lung cancer", Clinical Lung Cancer, 7(4):250-256 (Jan. 1, 2006).

Ma, Yanjun et al., "The role of the unfolded protein response in tumour development: friend or foe?", Nature Reviews. Cancer, 4(12):966-977 (Dec. 1, 2004).

* cited by examiner

| Probe Name | Fold change (KD vs. WT) | Regulation (KD vs. WT) | Gene Symbol | Description |
|---|---|---|---|---|
| A_23_P89431 | 242.71 | up | CCL2 | Homo sapiens chemokine (C-C motif) ligand 2 (CCL2), mRNA [NM_002982] |

A

B

C

LKB1 RELATED DIAGNOSTICS AND TREATMENTS OF CANCER

CROSS-REFERENCE TO RELATED APPLICATIONS

This application is a National Phase of International Application No. PCT/US2015/016304 filed Feb. 18, 2015, currently pending, which designated the U.S. and that International Application was published under PCT Article 21(2) in English. Both applications also include a claim of priority under 35 U.S.C. § 119(e) to U.S. provisional patent application No. 61/941,375 filed Feb. 18, 2014, the entirety of which is hereby incorporated by reference.

FIELD OF INVENTION

This invention relates to diagnosis and treatment of cancer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Non-small cell lung cancer (NSCLC) has become the leading cause of cancer-related deaths with a combined 5-year survival rate of only 16%. Among those with localized NSCLC, the survival rate is much higher at 52%; however, only 15% of lung cancers are diagnosed at this stage with 75% of cases involving metastasis at the time of diagnosis.

Accordingly, there remains a need in the art for methods for diagnosing and treating cancers including NSCLC.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method of diagnosing a cancer subtype in a subject, comprising: obtaining a sample from the subject; assaying the sample to determine the expression level of CCL2; assaying the sample to determine the expression level LKB1; and diagnosing the cancer subtype in the subject based on the presence of both level of CCL2 higher than a CCL2 reference level and a level of LKB1 lower than a LKB1 reference level.

In various embodiments, the method can further comprise assaying for the presence of activation of the mTORC1 complex. In various embodiments, the method can further comprise assaying for the presence of an upregulation of HIF1-α levels. In various embodiments, the method can further comprise assaying the expression level of CCL2 comprises detecting an increase in transcription of CCL2. In various embodiments, the method can further comprise assaying an increased sensitivity to endoplasmic reticulum (ER) stress.

In various embodiments, the cancer subtype can be non-small cell lung cancer (NSCLC).

Various embodiments of the present invention provide for a method of treating cancer in a subject in need thereof, comprising: diagnosing a sensitivity to pharmacological aggravation of ER stress in the subject; and treating the subject.

In various embodiments, diagnosing sensitivity to pharmacological aggravation of ER stress can be by detecting a loss of LKB1 expression in the subject. In various embodiments, diagnosing sensitivity to pharmacological aggravation of ER stress can be by detecting increases in phosphorylation of ER stress markers, and/or markers of ER stress mediated cell death In various embodiments, ER stress markers and markers of ER stress mediated cell death can be selected from the group consisting of phosphorylated eif2α, reactive oxygen species and cleaved caspase-9, cleaved PARP, phosphorylated IRE-1, XBP-1 splicing, phosphorylated H2AX and combinations thereof.

In various embodiments, the cancer can be NSCLC.

In various embodiments, treating the subject can comprise administering a therapeutically effective dosage of one or more compounds that target ER stress and/or the Unfolded Protein Response (UPR).

Various embodiments provide for a method of treating cancer in a subject in need thereof, comprising: diagnosing a tumor subtype in the subject; and treating the subject.

In various embodiments, the tumor subtype can be defined as KRas/LKB1-null.

In various embodiments, the cancer can be NSCLC.

In various embodiments, treating the subject can comprise administering a therapeutically effective dosage of a composition that can activate and/or aggravate ER stress.

In various embodiments, treating the subject can comprise administering a therapeutically effective dosage of tunicamycin, brefeldin A, 2DG, celecoxib, nelfinavir, 20S proteasome, heat shock protein 90 (HSP90) inhibitor, heat shock protein 70 (HSP70) inhibitor, autophagy inhibitor or combinations thereof. In various embodiments, the 20S proteasome can be bortezomib, MLN9708, or analogs thereof. In various embodiments, HSP90 inhibitor can be geldanamycin, BEP800, or analogs thereof. In various embodiments, the autophagy inhibitor can be VER155008.

In various embodiments, the tumor subtype can be characterized by low functional LKB1 expression. In various embodiments, the cancer can be lung adenocarcinoma. In various embodiments, the tumor cells can be under nutrient deprived conditions.

In various embodiments, the method can further comprise assaying for the expression level of CCL2 that is higher than a reference level.

Various embodiments provide for a method of diagnosing susceptibility to cancer in a subject, comprising: obtaining a sample from the subject; assaying the sample to determine the presence of a high level of CCL2; assaying the sample to determine the presence of a low LKB1; and diagnosing susceptibility to the cancer subtype in the subject based on the presence of both a high level of CCL2 and a low level of LKB1.

In various embodiments, the method can further comprise determining the presence of activation of the mTORC1 complex.

In various embodiments, the method can further comprise determining the presence of an upregulation of HIF1-α levels.

In various embodiments, the presence of a high level of CCL2 can be determined by detecting an increase in transcription of CCL2.

In various embodiments, the method can further comprise determining an increased sensitivity to endoplasmic reticulum (ER) stress.

In various embodiments, wherein the cancer can be non-small cell lung cancer (NSCLC).

Various embodiments provide for a method of prognosing cancer in an individual, comprising: obtaining a sample from the subject; assaying the sample to determine the presence of a high level of CCL2; assaying the sample to determine the presence of a low LKB1; and prognosing a severe form of cancer based on the presence of both a high level of CCL2 and a low level of LKB1.

In various embodiments, the method can further comprise determining an increased sensitivity to endoplasmic reticulum (ER) stress.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
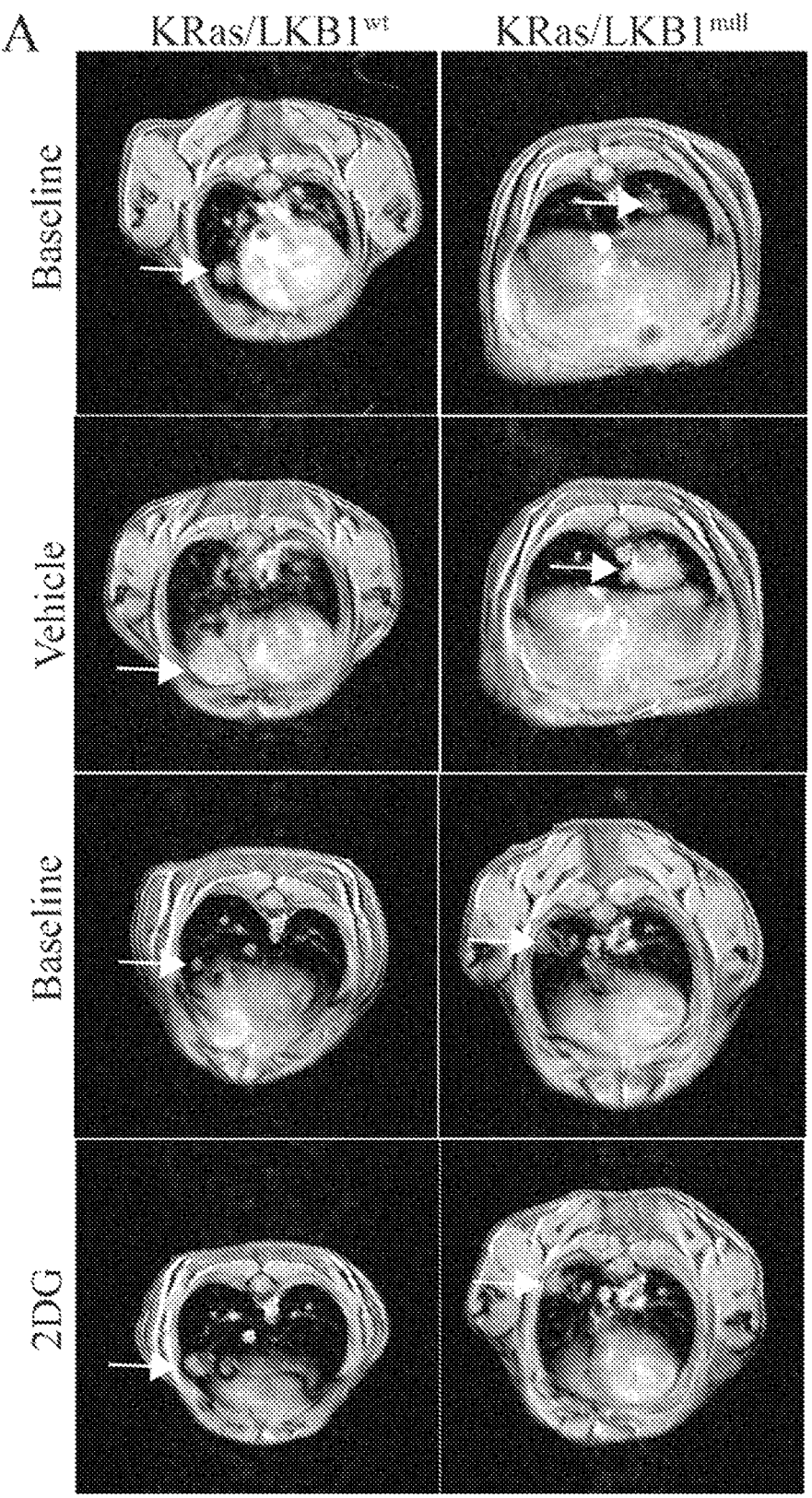
FIG. 1 shows, in accordance with embodiments herein, 2DG preferentially reduces the growth of LKB1-deficient NSCLC tumors. (A) Representative MRI images of NSCLC tumors in KRas/LKB1$^{wt}$ and KRas/LKB1$^{null}$ transgenic mice. KRas/LKB1$^{wt}$ and KRas/LKB1$^{null}$ transgenic mice underwent MRI imaging as described in herein to determine baseline and treated (vehicle, 2DG) tumor burden. White arrows indicated tumors encircled by a line. (B) Volumetric analysis of tumor volume in KRas/LKB1$^{wt}$ and KRas/LKB1$^{null}$ NSCLC tumors treated with vehicle (PBS) or 2DG (500 mg/kg, SID). Collected MRI images were analyzed as described in herein to determine the change in volume (baseline vs 3 weeks of treatment). Graphs depict the mean change in volume±SE of 5 mice in each group. P=0.0032.
Figure 1:
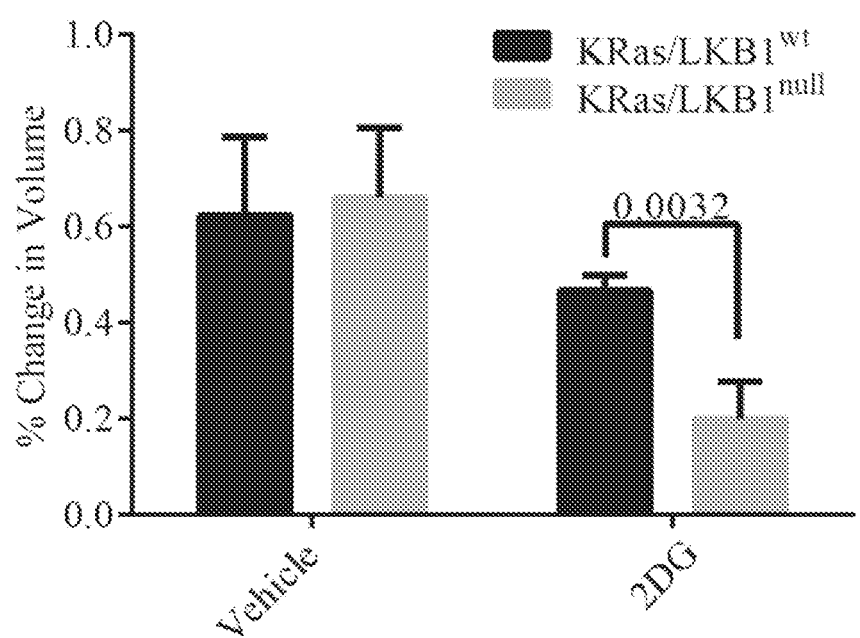

All references cited herein are incorporated by reference in their entirety as though fully set forth. Unless defined otherwise, technical and scientific terms used herein have the same meaning as commonly understood by one of ordinary skill in the art to which this invention belongs. Hornyak et al., Introduction to Nanoscience and Nanotechnology, CRC Press (2008); Singleton et al., *Dictionary of Microbiology and Molecular Biology* 3$^{rd}$ ed., Revised, J. Wiley & Sons (New York, N.Y. 2006); March, *Advanced Organic Chemistry Reactions, Mechanisms and Structure* 7$^{th}$ ed., J. Wiley & Sons (New York, N.Y. 2013); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

An "analog" as used herein refers to a molecule similar in function to either the entire molecule or to a fragment thereof. The term "analog" is also intended to include allelic species and induced variants. Analogs of peptides typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

Loss of the LKB1 tumor suppressor gene results in metastasis in transgenic mouse models and is associated with a poor prognosis and metastasis in human patients. Despite these observations, how LKB1 loss affects metastasis in NSCLC is poorly understood. In addition, evidence indicates an important role for the immune system in contributing to tumorigenesis and metastasis. Recruitment of monocytes is due to secretion of the chemokine CCL2. Although NSCLC and other solid tumors have been found to secrete increased levels of CCL2, the mechanism or mechanisms responsible for this observation is unknown. The inventors found that LKB1 loss results in increased expression and secretion of CCL2 in LKB1-null NSCLC cell lines. Furthermore, restoration of LKB1 expression within LKB1 null NSCLC ameliorates CCL2 expression and secretion. Investigation of signaling pathways deregulated within LKB1 null NSCLC cells supports increased activity of the mTORC1 complex as responsible for CCL2 expression. An explanation for this relationship could be the connection to HIF1-α. The mTORC1 complex is known to up-regulate HIF1-α, which has binding sites in the promoter region of CCL2. Consistent with this, the inventors found that the absence of LKB1 correlates with increased HIF1-α levels under normoxic conditions, suggesting that this increase in HIF1-α is responsible for increased CCL2. Collectively, these findings demonstrate a novel mechanism for how loss of LKB1 results in metastasis. Thus, the inventors have found that loss of LKB1 results in increased CCL2 secretion through the activation of mTOR, resulting in up-regulation of HIF1-alpha and the subsequent rise in CCL2 transcription, leading to increased monocyte recruitment and metastasis in NSCLC.

As further disclosed herein, the inventors found that LKB1 loss sensitizes non-small cell lung cancer cells to aggravation of ER stress. Five-year survival rates for non-small cell lung cancer (NSCLC) have seen minimal improvement despite aggressive therapy with standard chemotherapeutic agents, indicating a need for new treatment approaches. Inactivating mutations to the LKB1 tumor suppressor are common in NSCLC and are concurrent with activating mutations to the KRas oncogene. Genetic and mechanistic analyses of KRas/LKB1-null NSCLC tumors suggest that these tumors are a phenotypically distinct subpopulation of NSCLC and the unique features of KRas/LKB1-null tumors have potential for therapeutic gain. In the exploration of the mechanism(s) behind increased cytotoxicity of KRas/LKB1-null NSCLC cells to 2-D-Deoxyglucose (2DG), the inventors found that loss of LKB1 in NSCLC cells imparts increased sensitivity to pharmacological aggravation of ER stress. In a panel of NSCLC cell lines, LKB1 expression status correlated to differential expression of the ER stress markers, BiP and CHOP, with 2DG treatment. Treatment of isogenic LKB1-null NSCLC cells ectopically expressing LKB1 or a nonfunctional LKB1 with the ER stress activators, tunicamycin (Tm) or brefeldin A (BFA), revealed that expression of LKB1 increased cell viability and phosphorylation of AMPK. Conversely, isogenic LKB1-null NSCLC cells expressing nonfunctional LKB1 displayed increases in phosphorylation of the ER stress marker, eif2α and markers of ER stress mediated cell death (reactive oxygen species and cleaved caspase-9) following aggravation of ER stress with 2DG, Tm or BFA. The use of 2DG was effective in controlling the growth of KRas/LKB1-null tumors compared to KRas/LKB1-expressing tumors in transgenic NSCLC models and 2DG-treated KRas/LKB1-null NSCLC tumors displayed features consistent with 2DG treatment of in vitro KRas/LKB1-null NSCLC cell lines. Based upon these findings, it appears that KRas/LKB1-null NSCLC tumors are more sensitive to pharmacological aggravation of ER stress and therefore treatment for NSCLC patients whose tumors are defined as KRas/LKB1-null can be made.

We show herein that the non-hydrolyzable analog of glucose, 2DG has increased therapeutic efficacy in an in vivo model of LKB1-deficient NSCLC, compared to NSCLC tumors expressing LKB1. Studies directed towards elucidating the mechanism(s) behind the effect of 2DG in LKB1-deficient NSCLC tumors, reveal that the absence of LKB1 sensitizes NSCLC cells to aggravation of ER stress. Lack of LKB1 activity in NSCLC cells was associated with increased phosphorylation of eIF2a, CHOP and reduced survival, as well as evidence of UPR-mediated apoptosis (increased ROS, cleavage of caspase 9, reduced ATP). Significantly, these effects of 2DG in the absence of LKB1 also occurred upon aggravation of ER stress with Tm and BFA, two well-characterized inducers of ER stress. Further, treatment with celecoxib and bortezomib, two FDA approved compounds with ER stress activity, also displayed increased cytotoxicity when LKB1 activity was absent. Collectively, the sensitivity of LKB1-deficient NSCLC cells to ER stress aggravators (ERSAs) are suggestive of a potential treatment avenue for NSCLC and necessitate further studies.

Although our data suggests that LKB1-deficient NSCLC cells are hypersensitive to ERSAs, the mechanism behind this phenotype are unclear. One of LKB1's primary functions is alterations of cellular functions to restore ATP levels upon increased in AMP to promote cell survival. Thus the inability to activate LKB1 function and restore ATP levels upon ATF4/CHOP mediated depletion of ATP during ER stress in LKB1-deficient NSCLC cells is a plausible mechanism for our observations. However, LKB1 has been found to have broad regulatory functions, leading to a variety of alterations in cellular function when LKB1 is absent, in particular in initiation of autophagy, a catabolic mechanism responsible for degrading damaged organelles and proteins, via phosphorylation of the ULK1 kinase. Fittingly, autophagy is necessary for cell survival to ER stress, thought to alleviate proteo-toxicity via degradation of misfolded/unfolded proteins and the damaged ER. Thus, cytotoxicity of ERSAs in LKB1-deficient NSCLC cells could be a consequence of an inability to activate autophagy via failure to induce AMPK phosphorylation of ULK1, contributing to irremediable ER stress and activation of apoptosis. Consistent with this possibility, we found that 2DG, Tm and BFA results in ULK1 phosphorylation in only in H838-LKB1 cells (data not shown).

Figure 6:
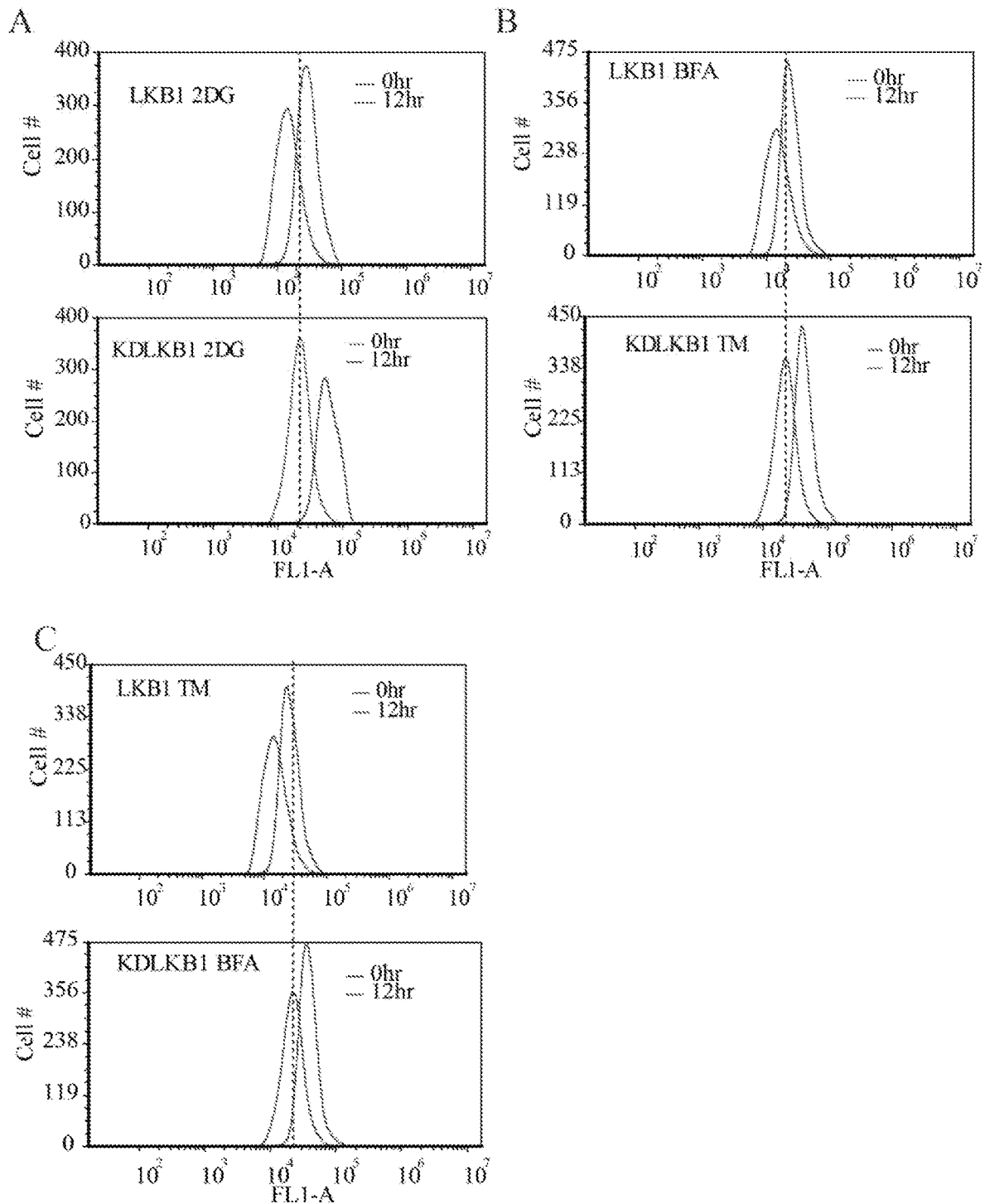
FIG. 6 depicts, in accordance with embodiments herein, ERSA treatment results in increased ROS levels in LKB1-deficient NSCLC cells. (A-C) Fluorescence-activated cell sorting (FACS) on H838-LKB1 (LKB1) and H838-KDLKB1 (KDLKB1) human NSCLC cells stained with CellROX™ following treatment with (A) 2DG (10 mM), (B) Tm (1.25 µg/ml) or (C) BFA (30 ng/ml) for twelve hours or at baseline (0 h). Dotted line highlights baseline (0 h) ROS levels in H838-KDLKB1 compared to ROS levels in H838-LKB1. H838-KDLKB1 displayed a 1.4-fold increase over H838-LKB1 at baseline and 2-fold (2DG), 1.2-fold (BFA) and 1.67-fold increase over H838-LKB1 with treatment. (D) LKB1-deficient H23 human NSCLC cells expressing full length LKB1 (H23-LKB1) or kinase dead LKB1 (H23-KDLKB1) were treated with celecoxib (40 1M) or bortezomib (40 nM) for 18 h. Protein lysates were immunoblotted with the indicated antibodies. (E) Clonogenic survival of H23-LKB1 and H23-KDLKB1 cells treated with vehicle (DMSO) or celecoxib or bortezomib at the indicated concentration for twenty-four hours. Surviving fraction was calculated as described in Material and Methods. Graph depicts mean±SE of three independent experiments.
Figure 6:
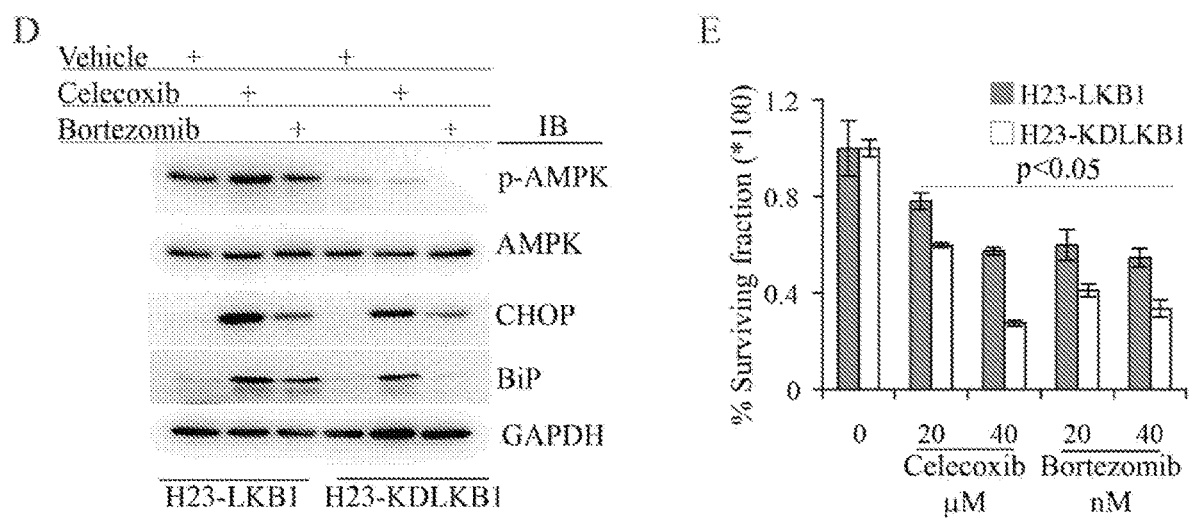
Figures 7, 8:
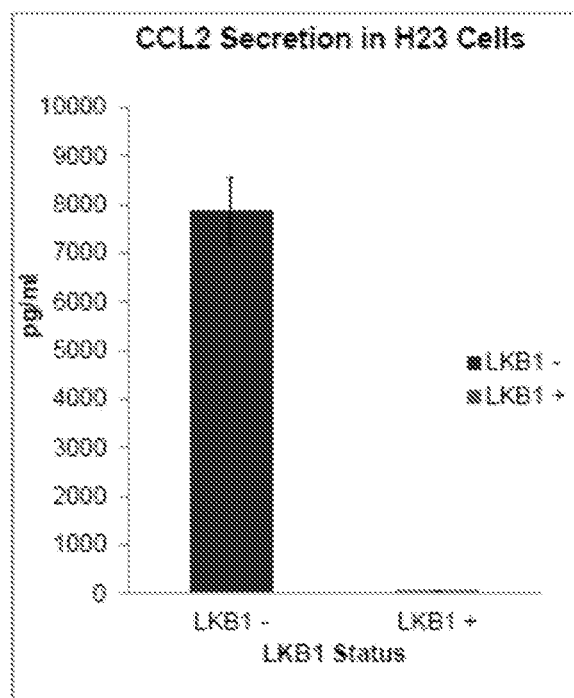
FIG. 7 depicts, in accordance with embodiments herein, gene microarray under Normoxic Conditions. Quantification of gene expression shows increase in CCL2 among Kinase-Dead H23 cells compared to Wildtype H23 cells.
FIG. 8 depicts, in accordance with embodiments herein, a graph of CCL2 ELISA with H23 cell line. Graph shows almost 8,000 pg/mL CCL2 being secreted from H23 LKB1-null cells and nearly 0 pg/mL by LKB1 Wildtype cell lines, suggesting LKB1 loss increases CCL2 secretion.
Figure 9:
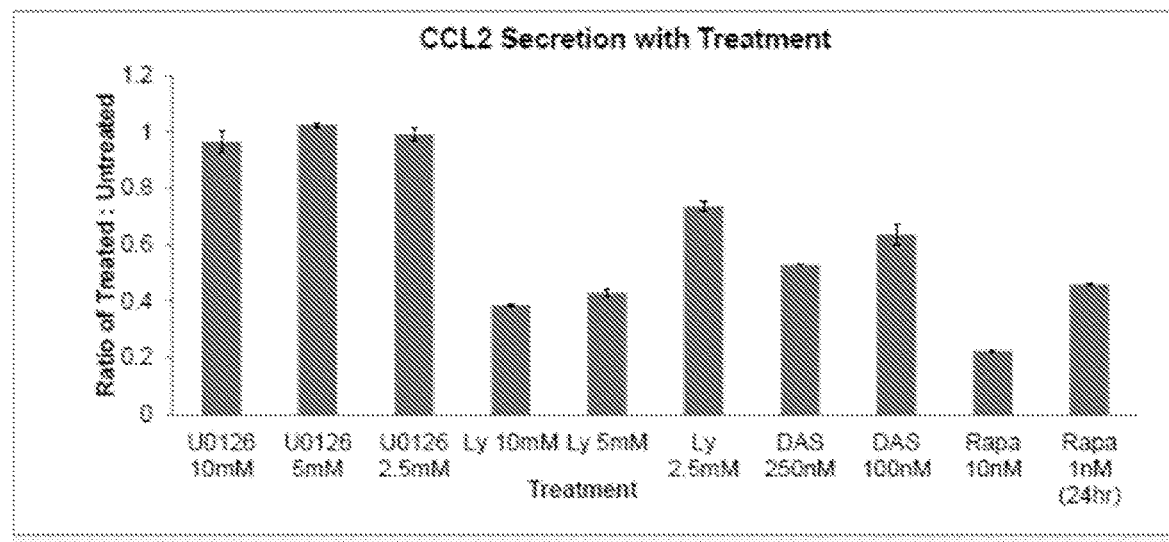
FIG. 9 depicts, in accordance with embodiments herein, an ELISA assay of H23 LKB1-null and LKB1-present cell lines treated with four different drug inhibitors. Rapamycin appears to have the strongest effect in decreasing CCL2 secretion.
Figure 10:
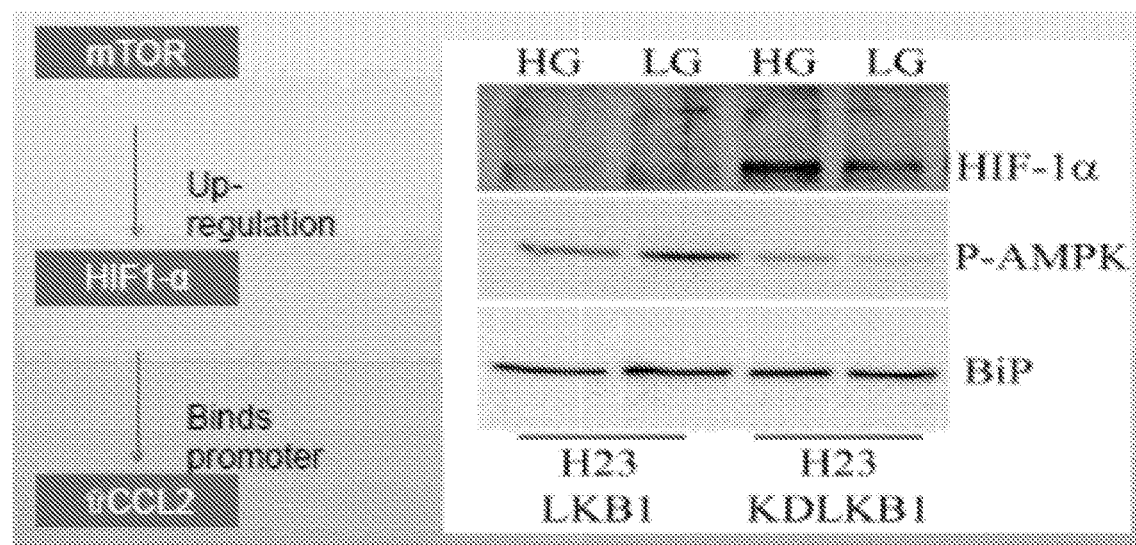
FIG. 10 depicts, in accordance with embodiments herein, a Western Blot of H23 LKB1 Kinase-Dead and LKB1 Wildtype cell lines under normoxic conditions. Blot shows HIF1-α to be highly upregulated in KD-LKB1 H23 cells vs. LKB1 H23 cells. Under high glucose conditions, there is an increase in HIF1-α. In H23 LkB1 cells there is more P-AMPK, the phosphorylated form of AMPK, the downstream target of LKB1. This suggests LKB1 loss results in increased HIF1-α and consequently increased CCL2 secretion.
Figure 11:
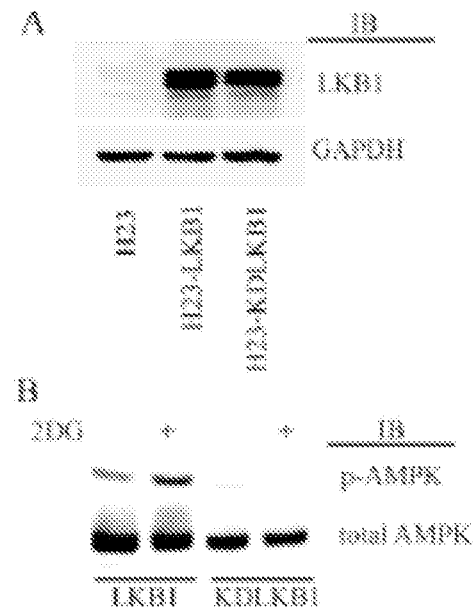
FIG. 11 depicts, in accordance with embodiments herein, expression of Kinase dead LKB1 (KDLKB1) and LKB1 in LKB1 null H23 NSCLC cells. A) Immunoblot for LKB1 in H23 parental, H23-LKB1, H23-KDLKB1 cells. B) Treatment of H23-LKB1 and H23-KDLKB1 with the AMPK agonist, 2DG. Note that 2DG treatment results in phosphorylation of AMPK (p-AMPK) when functional LKB1 is present, but KDLKB1 expression fails to result in p-AMPK
Figure 12:
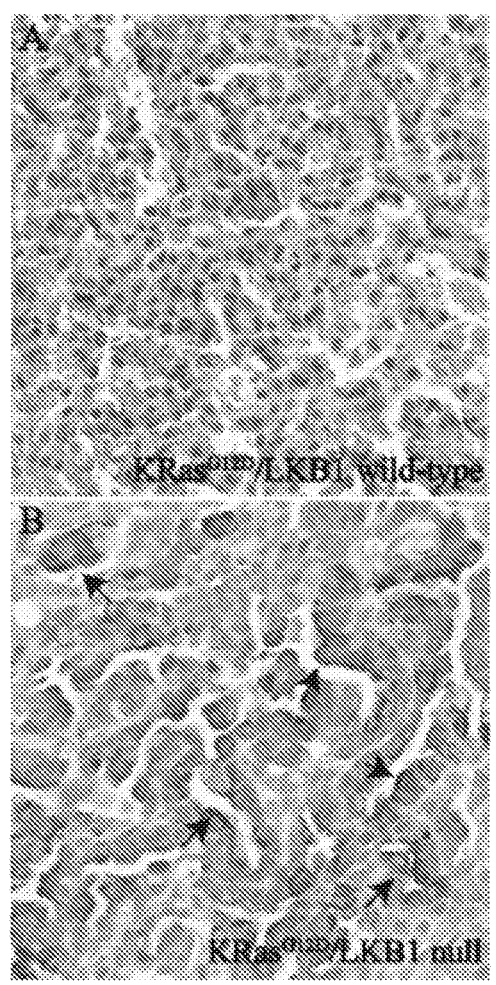
FIG. 12 depicts, in accordance with embodiments herein, representative images of CCL2 IHC staining in NSCLC tumors from transgenic KRasG12D/LKB1 wildtype (A) and KRasG12D/LKB1 null (B) mice. Arrows highlight CCL2 staining (Brown) in KRasG12D/LKB1 null NSCLC cells.
Figure 13:
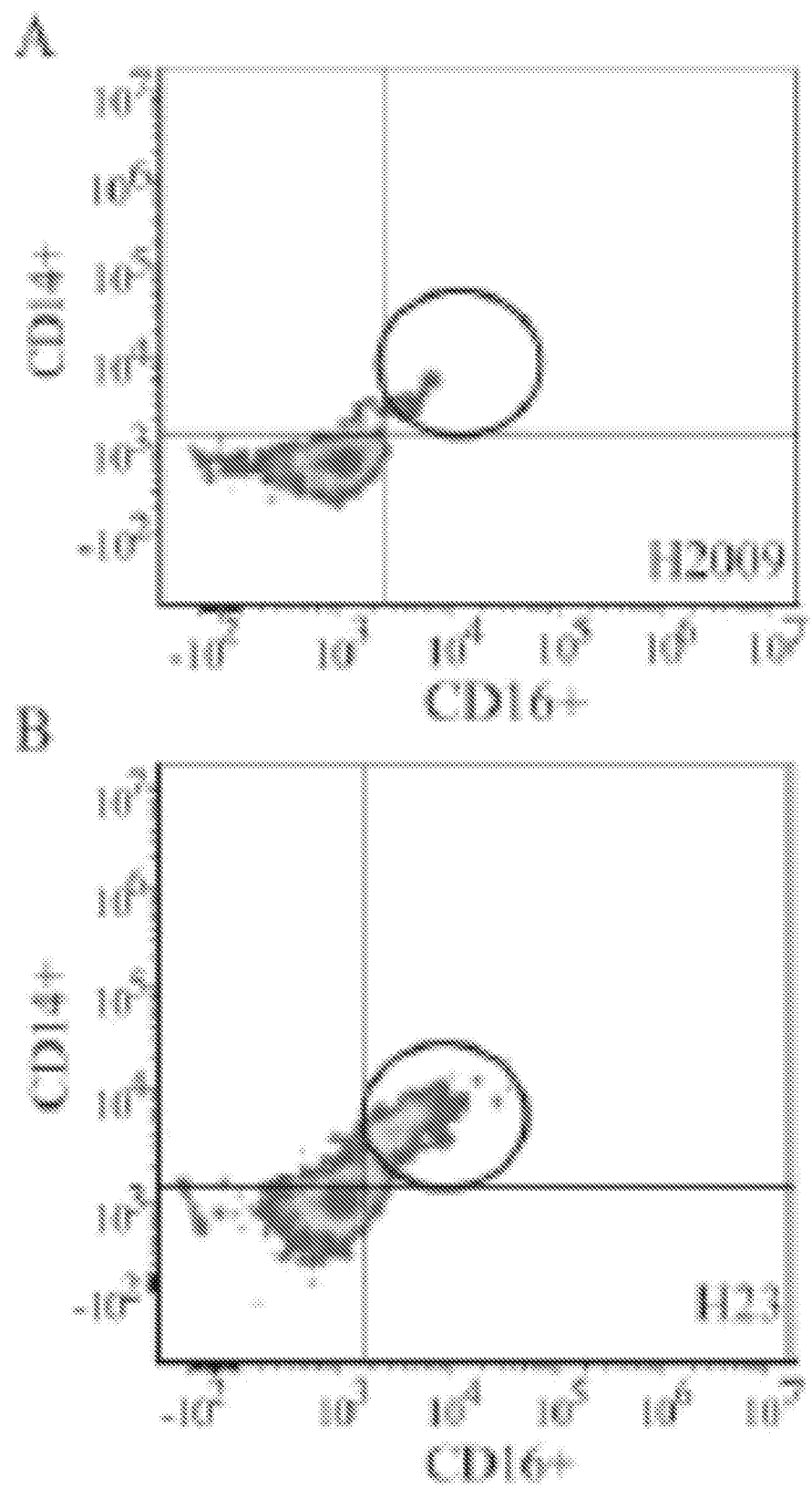
FIG. 13 depicts, in accordance with embodiments herein, flow cytometry analysis of migrated PBMCs present within the lower chamber following exposure to condition media from A) H2009 (LKB1 wild-type) or B) H23 (LKB1 null) NSCLC cells. Circle highlights the CD 16+, CD 14+ monocyte population.
Figure 14:
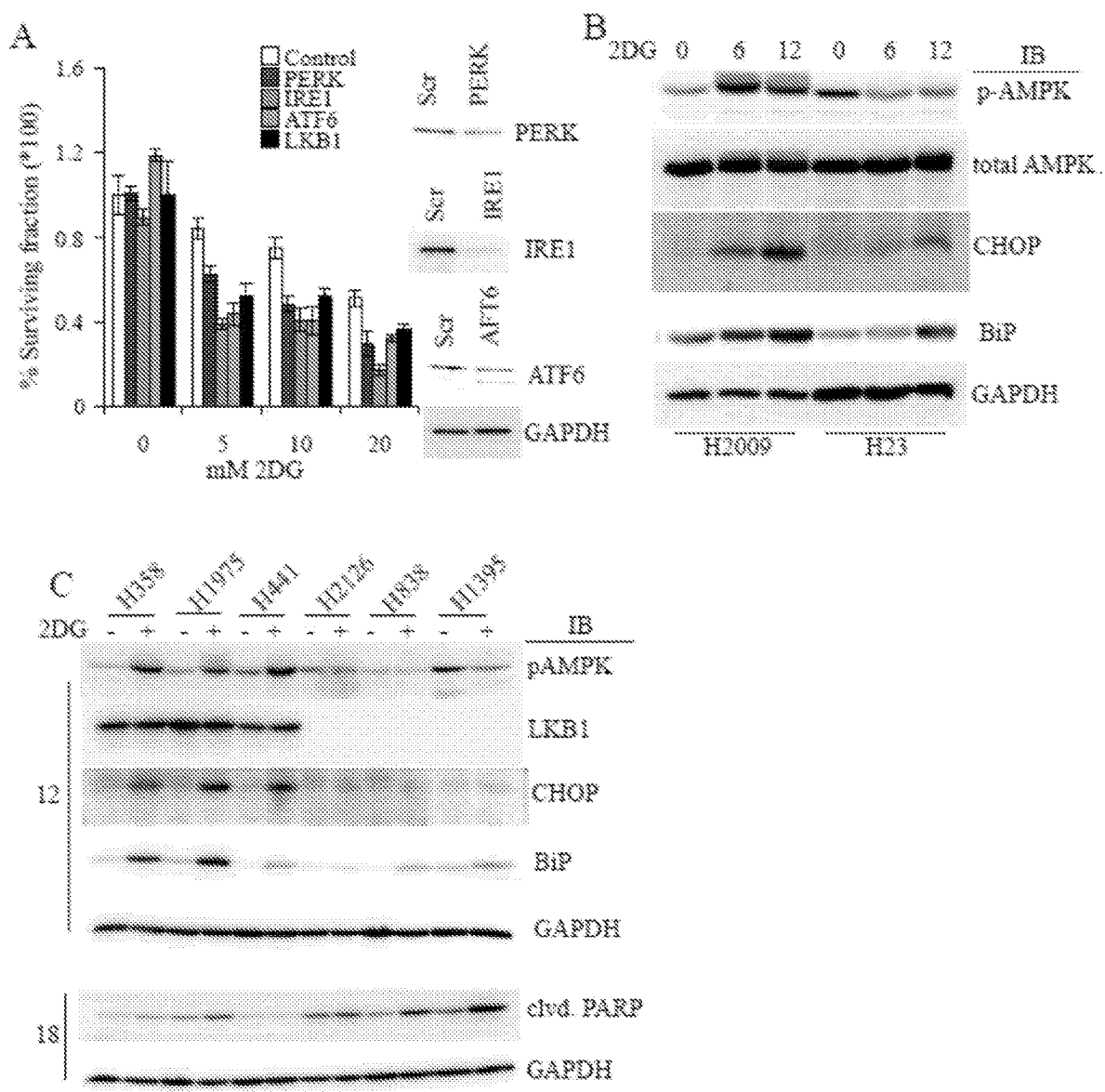
FIG. 14 depicts, in accordance with embodiments herein, reduced 2DG cytoxicity in LKB1 expressing LA cells correlates with increased UPR activation. A) Inhibition of UPR activation sensitizes LKB1 expressing H2009 LA cells to 2DG cytotoxicity in a clonogenic assay. LKB1 expressing H2009 LA cells were transfected with 100 nm of siRNA targeting PERK, IRE1, ATF6, LKB1 or scrambled control. siRNA transfected cells were plated for a clonogenic assay and treated for 24 hours with the indicated concentrations of 2DG. As expected, depletion of LKB1 sensitized H2009 cells to 2DG. Reduction of PERK, IRE1 and ATF6 also sensitized H2009 cells to 2DG. Depletion of PERK, IRE1, ATF6 and LKB1 were confirmed by immunoblot of remaining siRNA transfected cells following plating for clonogenic assay. Standard error bars represent the average of the mean of three independent experiments done in duplicate. B) LKB1 signaling correlates with increased activation of the UPR. LKB1 expressing H2009 or LKB1 null H23 LA cells were treated with 20 mM 2DG for the indicated times. Following SDS-PAGE, samples were immunoblotted for LKB1 phosphorylated AMPK and CHOP and BiP, markers of ER stress and the UPR. Note that LKB1 null H23 cells show decreased expression of CHOP and BiP, which correlates to loss of AMPK phosphorylation. GAPDH and total AMPK were used as loading controls. Blot is representative of 4 independent experiments. C) LKB1 expression correlates with increased activation of the UPR and decreased apoptosis in LA cells. A panel of LA cells (H358, H1975, H441-LKB1+; H2126, H838, H1395-LKB1−) was treated for 12 and 18 hours with 20 mM 2DG. Following SDS-PAGE, total protein lysates were immunoblotted with antibodies specific to LKB1, CHOP, BiP, phosphorylated AMPK and cleaved PARP, a marker of apoptosis. GAPDH was used as a loading control. Blot is representative of three independent experiments.
Figure 15:
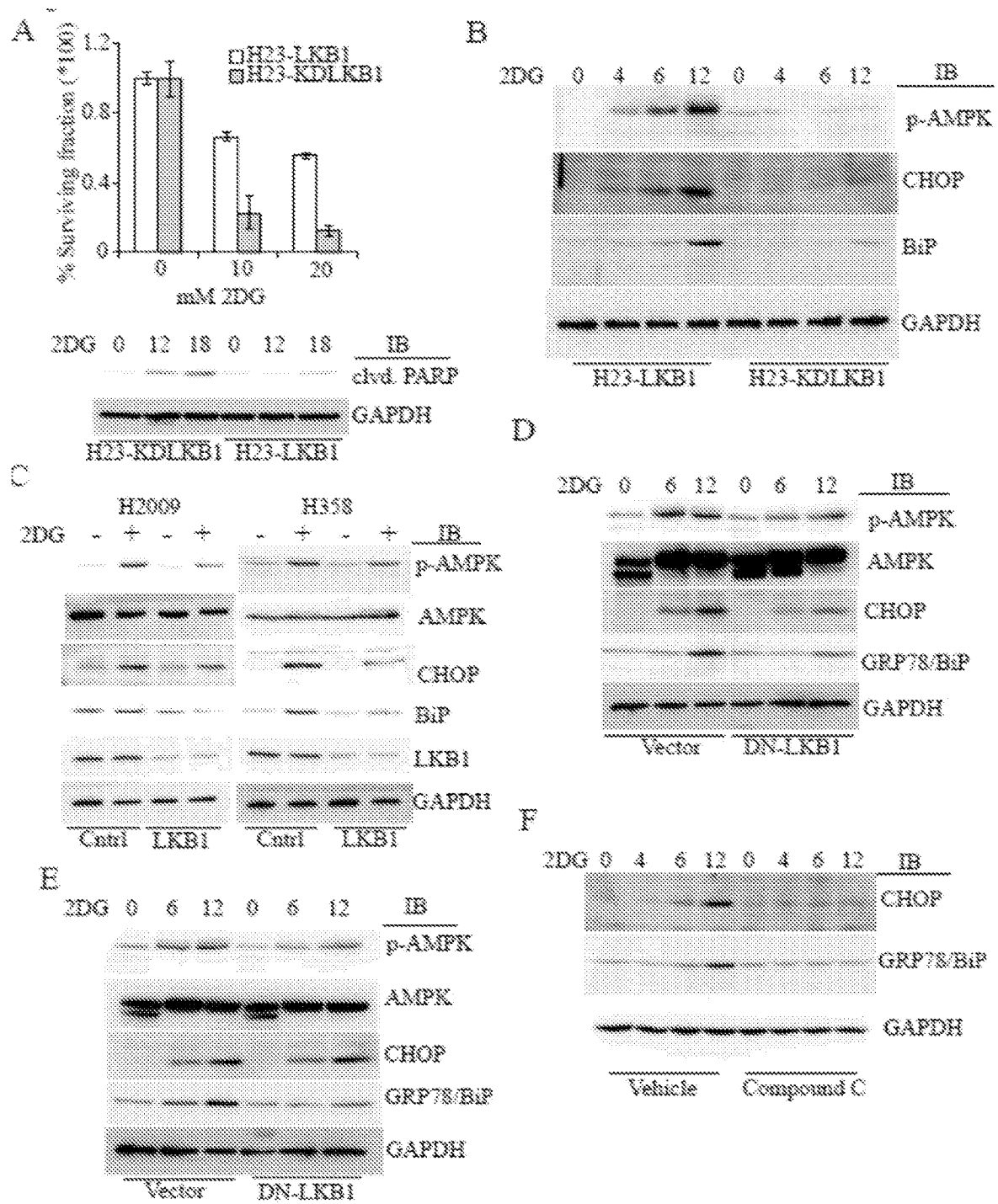
FIG. 15 depicts, in accordance with embodiments herein, LKB1-AMPK signaling is necessary for UPR activation in response to 2DG. A) Re-expression of LKB1 in LKB1 null H23 LA cell line reduces 2DG cytotoxicity. H23-LKB1 and H23-KDLKB1 LA cells were treated with 2DG and analyzed in a clonogenic assay (Top panel) and immunoblotting for cleaved PARP (Bottom panel). Standard error bars represent the average of the mean of three independent experiments done in duplicate. Blot is representative of three independent experiments. B) Re-expression of LKB1 in LKB1 null H23 LA cells restores activation of the UPR. H23-LKB1 and H23-KDLKB1 LA cells were treated with 20 mM 2DG for the indicated times and probed. Re-expression of LKB1 restores AMPK activation and expression of UPR markers (CHOP, BiP). GAPDH and total AMPK were used as loading controls. Blot is representative of 4 independent experiments. C) Reduction of LKB1 by siRNA knockdown attenuates UPR activation. LKB1 expressing H2009 or H358 were transfected with 100 nM siRNA targeting human LKB1 or a scrambled control. 48 hours after transfection, cells were treated with 20 mM 2DG for 6 hours, before SDS-PAGE and immunoblot analysis of CHOP, BiP, phosphorylated AMPK and LKB1 protein levels. Note that reduced LKB1 levels correlate with reduction in CHOP and BiP protein levels. GAPDH was used as a loading control. Blot is representative of 3 independent experiments. D, E, F) Inhibition of AMPK activation reduces UPR activation. D, E) H2009 (D) and H358 (E) LA cells were infected with a dominant negative LKB1 retroviral construct (DN-LKB1) or empty vector (Vector). Following puromycin selection, cells were treated with 20 mM 2DG for the indicated times and probed for phosphorylated AMPK, CHOP and BiP protein levels. Reduced AMPK activation by DN-LKB1 attenuates protein levels of BiP and CHOP. GAPDH and total AMPK were used as loading controls. Blot is representative of 4 independent experiments. F) LKB1 expressing H2009 LA cells were pretreated with the AMPK inhibitor Compound C at 20 mM, before treatment with 20 mM 2DG for the indicated times. Attenuation of AMPK activity results in reduction of CHOP and BiP protein levels. GAPDH was used as loading controls. Blot is representative of 4 independent experiments.
Figure 16:
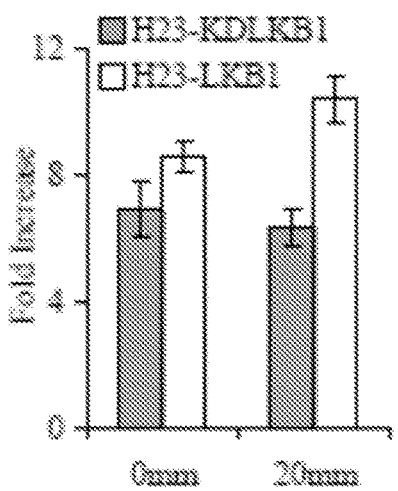
FIG. 16 depicts, in accordance with embodiments herein, LKB1 correlates with increased ATF6. A) LKB1 does not affect PERK phosphorylation of eif2α or IRE1 dependent splicing of XBP-1. H23-LKB1 and H23-KDLKB1 LA cells were treated with 20 mM 2DG for the indicated times before analysis of phosphorylated eif2α (top panel) and unprocessed (XBP-1u) and spliced (XBP-1s) XBP-1 mRNA (bottom panel). Total eif2 and actin were used as a loading control. Blot and gel are representative of 4 independent experiments. B) H23-LKB1 and H23-KDLKB1 cells were treated with 2DG for 6 hours before isolation of total protein or nuclear lysates. Total protein lysates and nuclear protein fractions of 2DG treated and untreated H23-LKB1 and H23-KDLKB1 LA cells were immunoblotted with an antibody that recognizes cleaved (active) ATF6. Note that 2DG treatment results in increased cleaved ATF6 in H23-LKB1, but not H23-KDLKB1. GAPDH and Lamin A/C were used as loading controls, respectively. Blot is representative of three independent experiments. C) H23-LKB1 and H23-KDLKB1 were treated with 5 ug/ml Tunicamycin for 6 hours and analyzed as in A). Note active ATF6 only increases in H23-LKB1, but not H23-KDLKB1 cells.
Figure 16:
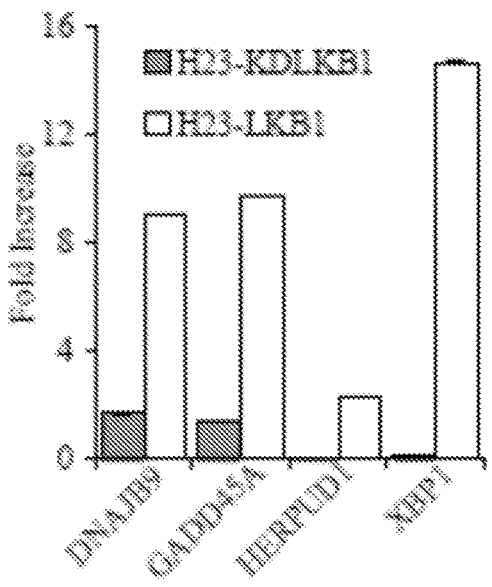
Figure 16:
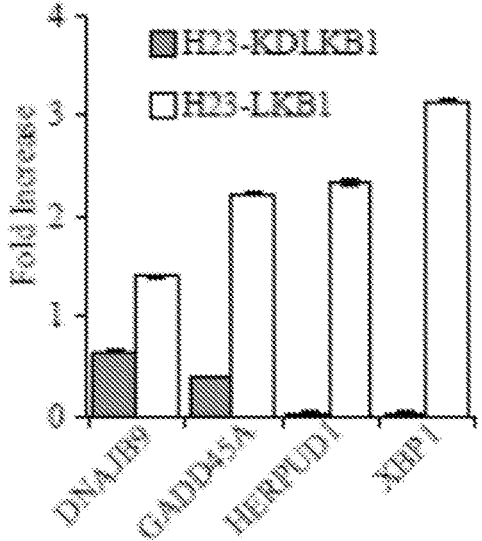
Figure 17:
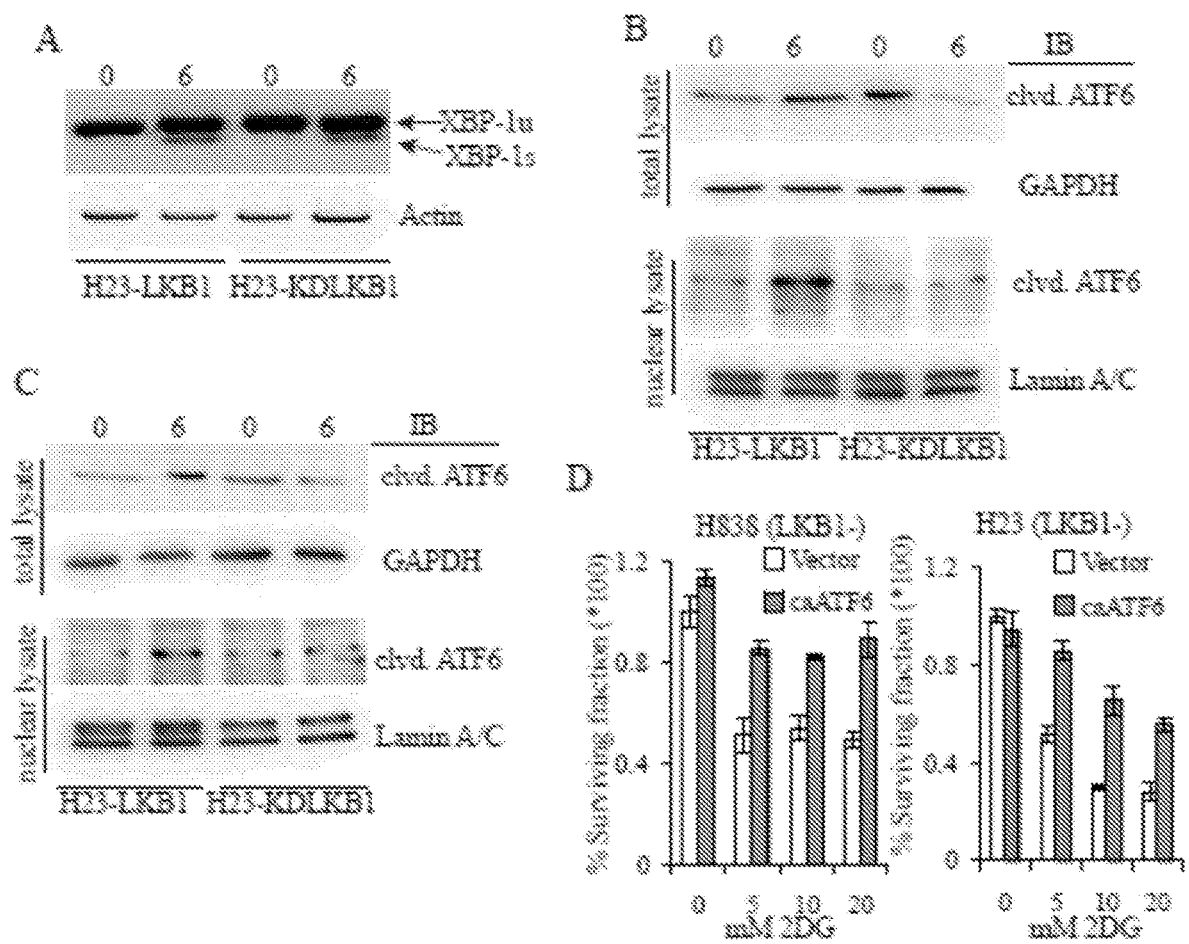
FIG. 17 depicts, in accordance with embodiments herein, LKB1 increases UPR mediated transcription in response to 2DG. A) H23-LKB1 and H23-KDLKB1 LA cells were transfected with the ERSE and Renilla reporters. Cells were treated with 20 mM 2DG for 6 hours before analysis of luciferase levels. Standard error bars represent the average of the mean of two independent experiments done in octuplicate. B) qPCR of ATF6 target genes, HERPUD1 and XBP1 in H23-LKB1 and H23-KDLKB1 cells treated with 2DG for 18 hours. Fold change of HERPUD1 and XBP1 corresponds to change in gene expression in treated cells relative to untreated samples, following normalization of treated and untreated gene expression to GAPDH control gene. Error bars represent average to two independent experiments done in triplicate. C) qPCR analysis of ATF6 target genes HERPUD1 and XBP1 in H23-LKB1 and H23-KDLKB1 cells treated with tunicamycin for 18 hours. Fold change in expression of HERPUD1 and XBP1 were analyzed and calculated as in B. D) Expression of constitutively active ATF6 (caATF6, aa 1-373) in LKB1 null LA cells (H838, H23) reduces 2DG cytotoxicity in a clonogenic assay. H23 and H838 were transfected with pGCN-caATF6 or empty vector and plated for clonogenic assays. Expression of caATF6 reduced the cytotoxic effects of 2DG within both H838 and H23 LKB1 null LA cell lines. Expression of HA-tagged caATF6 was confirmed by immunoblotting for HA tag in remaining cells following plating for clonogenic assays. Standard error bars represent the average of the mean of three independent experiments done in duplicate.
Figures 18, 19:
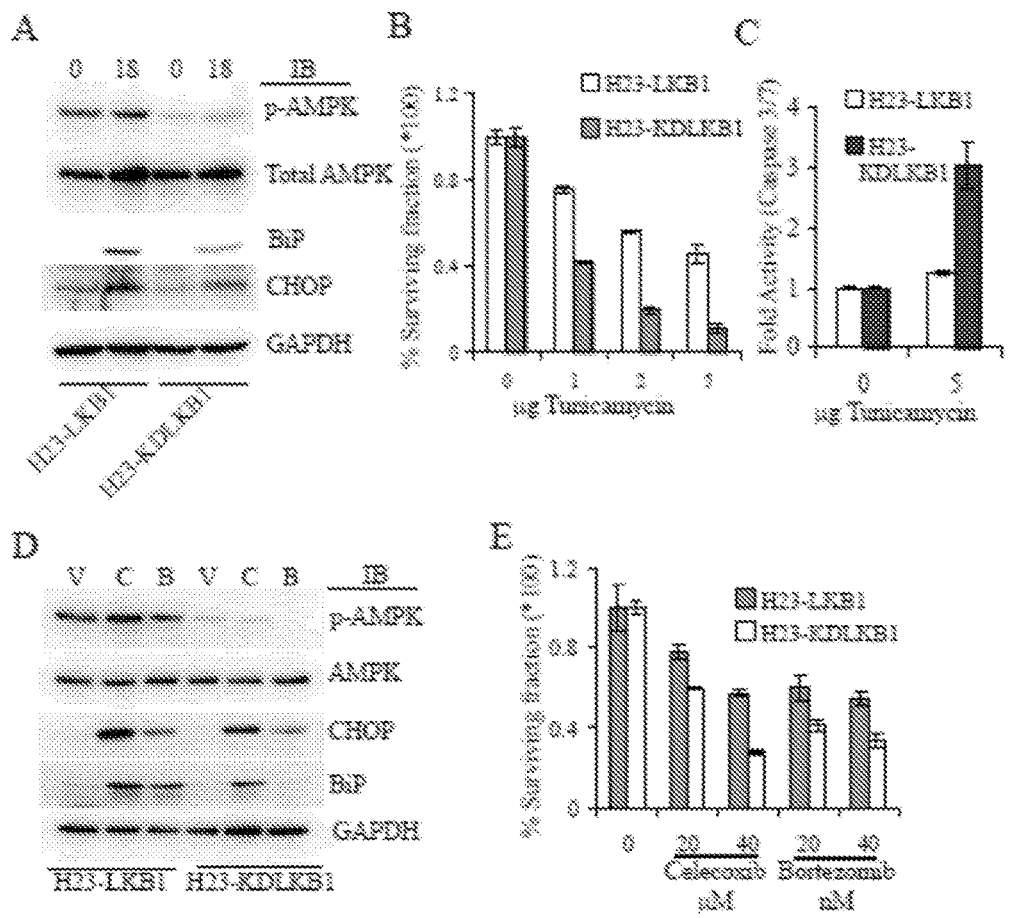
FIG. 18 depicts, in accordance with embodiments herein, LKB1 attenuates cytoxicity due to pharmacological aggravation of UPR. A) H23-LKB1 and H23-KDLKB1 were treated with 5 ug/ml tunicamycin and lysed at the indicated times. Total protein lysates were probed for expression of phosphorylated AMPK, CHOP and BiP. Treatment with tunicamycin resulted in increased CHOP and BiP expression in H23-LKB1 cells relative to H23-KDLKB1. GAPDH and total AMPK were used as loading controls. Blot is representative of three independent experiments. B) Effect of tunicamycin upon survival in H23-LKB1 and H23-KDLKB1 LA cells. H23-LKB1 and H23-KDLKB1 were treated with tunicamycin at the indicated concentrations for 24 hours and survival assessed in clonogenic assays. Expression of LKB1 ameliorated tunicamycin cytotoxicity compared to expression of kinase dead KDLKB1. Standard error bars represent the average of the mean of four independent experiments done in triplicate. C) LKB1 reduces activation of apoptosis by tunicamycin in H23 LA cells. H23-LKB1 and H23-KDLKB1 LA cells were treated with 5 ug/ml tunicamycin for 24 hours before activation of apoptosis was assessed by measurement of activity of Caspases 3 and 7. H23-KDLKB1 display increased levels of Caspase activity with tunicamycin treatment. Standard error bars represent the average of the mean of two independent experiments. D) LKB1 reduces cytoxic effects of ER stress activators, celecoxib and bortezomib. H23-LKB1 and H23-KDLKB1 LA cells were treated with indicated concentrations of either vehicle (DMSO), celecoxib or bortezomib for 24 hours followed by lysis. Total protein lysates were separated by SDS-PAGE and probed with antibodies specific to phosphorylated AMPK, CHOP and BiP. Both celecoxib and bortezomib treatment resulted in increased expression of CHOP and BiP in H23-LKB1 cells, which correlated with phosphorylated AMPK. E) H23-LKB1 and H23-KDLKB1 LA cells were treated with indicated concentrations of either vehicle, celecoxib or bortezomib for 24 hours in clonogenic assays. H23-KDLKB1 displayed increased sensitivity to celecoxib and bortezomib cytotoxicity, relative to H23-LKB1 LA cells. Standard error bars represent the average of the mean of three independent experiments done in triplicate.
FIG. 19 depicts, in accordance with embodiments herein, a table showing LKB1 increases transcription of UPR target genes. Tabular results of microarray analysis of LKB1 expressing H2009 (LKB1+) or LKB1 null H23 (LKB1−) LA cell lines treated or untreated, in a dose dependent manner, with 2DG for 6 hours at either 2.5 mM or 20 mM. Shown is a subset of genes involved in the UPR based upon published literature that were found to be statistically significant (corrected p<0.05) by t-test and differentially expressed at least two-fold between LKB+ and LKB1− cell lines at two concentrations of 2DG treatment. Those displaying N/C (No Change) did not demonstrate statistically significant changes in expression.

Our in vitro data suggest that ERSA treatment may have efficacy in LKB1-deficient NSCLC tumors. Although daily treatment with 2DG was found to have increased efficacy in LKB1-deficient NSCLC tumors, compared to NSCLC tumors with functional LKB1 (FIG. 1), we found 2DG had no observable effects upon metastasis in KRas/LKB1$^{null}$ mice. As metastasis is the major cause of cancer related mortalities, this finding which would also explain why 2DG had no statistical impact upon survival in KRas/LKB1$^{null}$ mice in longer term studies (data not shown). Further, we found that chronic dosing with 2DG or Tm was poorly tolerated, consistent with published reports of toxic side effects. Collectively, these observations indicate that 2DG may display greater efficacy if used in defined combinations instead of as a single agent or in combination with standard treatments. Alternatively, it would be more useful to assess the effects of ERSAs with established clinical profiles. Currently several compounds with known ERSA effects are approved by the FDA, most notably are bortezomib, celecoxib and nelfinavir. Indeed, we found that both bortezomib and celecoxib displayed increased in vitro cytotoxicity within an isogenic LKB1-deficient NSCLC cell line (FIG. 6E). Mechanistically, celecoxib has been shown to induce ER stress by causing calcium efflux from the ER due to inhibition of the sarcoplasmic/endoplasmic reticulum calcium ATPase, in addition to its known ability to inhibit COX-2. Celecoxib's ERSA activity has been theorized as a possible mechanism for its antitumor effects, however the considerable cardiovascular side effects associated with celecoxib, and its lack of antitumor in advanced tumors, has led to studies aimed at developing analogs of celecoxib with more potent ERSA activity and eliminating its COX-2 inhibitory function. ERSA activity of both bortezomib and nelfinavir are based upon their functions in inhibiting proteasomal degradation. Nelfinavir, currently approved for treatment of HIV infections, has been found to have considerable antitumor activity, inducing cytotoxicity as a single agent, as well as enhancing the toxicity of standard treatments. As such, clinical trials for nelfinavir are ongoing. Although bortezomib has considerable activity towards hematologic malignancies, it has minimal activity in solid tumors, due its inability to penetrate tissues and achieve efficacious concentrations. Several second generation proteasome inhibitors have been developed, such as MLN9708, which displays improved tissue distribution and antitumor activity in solid tumors, and represent an attractive alternative to bortezomib in treating LKB1-deficient NSCLC.

Diagnosis

In various embodiments, the present invention provides a method of diagnosing a cancer subtype in a subject, comprising obtaining a sample from the subject, assaying the sample to determine the presence of a high level of CCL2, assaying the sample to determine the presence of a low LKB1, and diagnosing the cancer subtype in the subject based on the presence of both a high level of CCL2 and a low level of LKB1. In another embodiment, the present invention further comprises determining the presence of activation of the mTORC1 complex. In another embodiment, the present invention further comprises determining the presence of an upregulation of HIF1-α levels. In another embodiment, the presence of a high level of CCL2 is determined by detecting an increase in transcription of CCL2. In another embodiment, the present invention further comprises determining an increased sensitivity to endoplasmic reticulum (ER) stress. In another embodiment, the cancer subtype is non-small cell lung cancer (NSCLC).

In various embodiments, the present invention provides a method of diagnosing susceptibility to cancer in a subject, comprising obtaining a sample from the subject, assaying the sample to determine the presence of a high level of CCL2, assaying the sample to determine the presence of a low LKB1 and diagnosing susceptibility to the cancer subtype in the subject based on the presence of both a high level of CCL2 and a low level of LKB1. In another embodiment, the present invention further comprises determining the presence of activation of the mTORC1 complex. In another embodiment, the present invention further comprises determining the presence of an upregulation of HIF1-α levels. In another embodiment, the presence of a high level of CCL2 is determined by detecting an increase in transcription of CCL2. In another embodiment, the present invention further comprises determining an increased sensitivity to endoplasmic reticulum (ER) stress. In another embodiment, the cancer is non-small cell lung cancer (NSCLC).

Various embodiments provide for a method of diagnosing non-small cell lung cancer (NSCLC), comprising: obtaining a biological sample from a subject; assaying the sample to determine the expression level of LKB1; and diagnosing NSCLC if the LKB1 expression level is lower than a LKB1 reference level.

In various embodiments, the method further comprises assaying the sample to determine the expression level of CCL2; and diagnosing NSCLC if the CCL2 expression level is higher than a CCL2 reference level and the LKB1 expression level is lower than a LKB1 reference level. In various embodiments, assaying the expression level of CCL2 comprises detecting an increase in the transcription of CCL2.

In various embodiments, the method further comprises assaying for the presence of an upregulation of HIF1-alpha levels.

Prognosis

In various embodiments, the present invention provides a method of prognosing cancer in an individual, comprising obtaining a sample from the subject, assaying the sample to determine the presence of a high level of CCL2, assaying the sample to determine the presence of a low LKB1; and prognosing a severe form of cancer based on the presence of both a high level of CCL2 and a low level of LKB1. In another embodiment, the present invention further comprises determining an increased sensitivity to endoplasmic reticulum (ER) stress.

Selection of Treatment

Various embodiments provide for a method of selecting treatment for cancer, comprising: obtaining a biological sample from a subject; assaying the sample to determine the expression level of LKB1; and selecting an endoplasmic reticulum stress activators if the LKB1 expression level is lower than a LKB1 reference level.

Various embodiments provide for a method of selecting treatment for cancer, comprising: obtaining a biological sample from a subject; assaying the sample to determine sensitivity to pharmacological aggravation of ER stress; and selecting an endoplasmic reticulum stress activators if the sensitivity is detected.

In various embodiments, detecting sensitivity comprises detecting an increase in phosphorylation of ER stress markers and/or markers of ER stress mediated cell death. Examples of these markers include but are not limited to phosphorylated eif2-alpha, reactive oxygen species, cleaved caspase-9, cleaved PARP, phosphorylated IRE-1, XBP-1 splicing, and phosphorylated H2AX.

In various embodiments, the cancer is non-small cell lung cancer (NSCLC). In other embodiments, the cancer is lung adenocarcinoma. In still other embodiments, the cancer is a KRas/LKB1-null cancer.

Treatment

In various embodiments, the present invention provides a method of treating a cancer, comprising diagnosing a sensitivity to pharmacological aggravation of ER stress in the subject, and treating the subject. In another embodiment, diagnosing sensitivity to pharmacological aggravation of ER stress is determined by detecting a loss of LKB1 expression in the subject. In another embodiment, diagnosing sensitivity to pharmacological aggravation of ER stress is determined by detecting increases in phosphorylation of ER stress markers, such as eif2α, and/or markers of ER stress mediated cell death, such as reactive oxygen species and cleaved caspase-9. In another embodiment, the cancer is NSCLC.

In various embodiments, the present invention provides a method of treating a cancer, comprising diagnosing a tumor subtype in the subject, and treating the subject. In another embodiment, the tumor subtype is defined as KRas/LKB1-null. In another embodiment, the cancer is NSCLC. In another embodiment, the subject is treated by administering a therapeutically effective dosage of a composition that can activate and/or aggravate ER stress. In another embodiment, the subject is treated by administering a therapeutically effective dosage of celecoxib, bortzemib, 2-D-deoxyglucose, and/or tunicamycin. In another embodiment, the tumor subtype is characterized by low functional LKB1 expression. In another embodiment, the cancer is lung adenocarcinoma. In another embodiment, the tumor cells are under nutrient deprived conditions such as low glucose. In another embodiment, the present invention further comprises determining a high level of CCL2 expression.

Various embodiments provide for a method of treating a cancer, comprising: obtaining a biological sample from a subject; assaying the sample to determine the expression level of LKB1; and treating the cancer with an endoplasmic reticulum stress activator if the LKB1 expression level is lower than a LKB1 reference level.

In various embodiments, the cancer is non-small cell lung cancer (NSCLC). In other embodiments, the cancer is lung adenocarcinoma. In still other embodiments, the cancer is a KRas/LKB1-null cancer.

In various embodiments, the present invention provides a composition comprising one or more inhibitors of CCL2 secretion, and an acceptable carrier. In another embodiment, the one or more inhibitors of CCL2 secretion inhibits mTORC1 complex activity. In another embodiment, the one or more inhibitors of CCL2 secretion inhibits HIF1-α activity. In another embodiment, the one or more inhibitors of CCL2 secretion includes LKB1. In another embodiment, the present invention provides a method of treating cancer by administering a therapeutically effective dosage of a composition comprising one or more inhibitors of CCL2 secretion.

In various embodiments, the present invention provides a composition comprising one or more compounds that aggravate ER stress, and an acceptable carrier. In another embodiment, the present invention provides a method of treating cancer in a subject by administering a therapeutically effective dosage of the composition comprising one or more compounds that aggravate ER stress and an acceptable carrier to the subject.

Endoplasmic Reticulum Stress Activators (ERSAs)

Examples of ERSAs that can be selected or administered in accordance with various embodiments of the present invention include but are not limited to tunicamycin, brefeldin A, 2DG, celecoxib, nelfinavir, 20S proteasome (bortezomib, MLN9708 and analogs thereof). Additional examples include but are not limited to inhibitors of heat shock protein 90 (geldanamycin and analogs, BEP800), HSP70 (VER155008 and others), and inhibitors of autophagy.

Reference Values

In various embodiments, the reference value can be the median or mean expression level of the gene of interest (e.g., LKB1, CCL2, HIF1-alpha, KRas, housekeeping gene used as a reference gene) from a population of subjects with an intact gene, or a population of subjects without cancer. In various embodiments, the reference value can be from the subject's own blood, serum, or plasma sample; for example, when the biological sample that is assayed is tumor or cancer cells or tumor or cancer tissue.

The nucleic acid samples used to compute a reference value when taken from a population of subjects are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine gene expression can be fragments of genomic nucleic acid generated by restriction enzyme digestion and/or ligation to other nucleic acid, and/or amplification products of genomic nucleic acids, pre-messenger RNA (pre-mRNA), or post-messenger RNA (the mature form of mRNA), amplification products of pre- or post-mRNA, or genomic DNA fragments grown up in cloning vectors generated, e.g., by "shotgun" cloning methods. In certain embodiments, genomic nucleic acid samples are digested with restriction enzymes.

Housekeeping Genes

In various embodiments, the reference value can be the expression of a house keeping gene (See e.g., Eisenberg and Levanon, Human housekeeping genes are compact. Trends in Genetics, Volume 19, Issue 7, 362-365, 1 Jul. 2003; Valeria Valente et al., RefGenes: identification of reliable and condition specific reference genes for RT-qPCR data normalization (2011), BMC Genomics). Examples of housekeeping genes include, but are not limited to beta-actin, histone H3, and 28S ribosomal RNA. One of ordinary skill in the art can easily determine what the cut-off points for increased expression for any one of these genes are.

Assays

In various embodiments, assaying or determining the expression level comprise using DNA sequencing, comparative genomic hybridization (CGH), array CGH (aCGH), SNP analysis, mRNA expression assay, RT-PCR, real-time PCR, or a combination thereof.

In various embodiments, assaying or determining the expression level comprises using ELISA, immunohistochemistry, flow cytometry, fluorescence in situ hybridization (FISH), radioimmunoassays, affinity purification or combinations thereof.

Biological Samples

Examples of biological sample that can be tested or assays in accordance with various embodiments of the present invention include, but are not limited to tumor cells, tumor tissue, cancer cells, cancer tissue, mammalian body fluids, sera such as blood (including whole blood as well as its plasma and serum), CSF (spinal fluid), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysates, hair, skin, buccal scrapings, nails, bone marrow, cartilage, prions, bone powder, ear wax, etc. or even from external or archived sources such as tumor samples (i.e., fresh, frozen or paraffin-embedded).

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

LKB1 and CCL2

Non-small cell lung cancer (NSCLC) has become the leading cause of cancer-related deaths with a combined 5-year survival rate of only 16%. Among those with localized NSCLC, the survival rate is much higher at 52%; however, only 15% of lung cancers are diagnosed at this stage with 75% of cases involving metastasis at the time of diagnosis. Loss of the LKB1 tumor suppressor gene results in metastasis in transgenic mouse models and is associated with a poor prognosis and metastasis in human patients. Despite these observations, how LKB1 loss affects metastasis in NSCLC is poorly understood. In addition, evidence indicates an important role for the immune system in contributing to tumorigenesis and metastasis. Recruitment of monocytes is due to secretion of the chemokine CCL2. Although NSCLC and other solid tumors have been found to secrete increased levels of CCL2, the mechanism or mechanisms responsible for this observation is unknown. The inventors found that LKB1 loss results in increased expression and secretion of CCL2 in LKB1-null NSCLC cell lines. Furthermore, restoration of LKB1 expression within LKB1 null NSCLC ameliorates CCL2 expression and secretion. Investigation of signaling pathways deregulated within LKB1 null NSCLC cells supports increased activity of the mTORC1 complex as responsible for CCL2 expression. An explanation for this relationship could be the connection to HIF1-α. The mTORC1 complex is known to up-regulate HIF1-α, which has binding sites in the promoter region of CCL2. Consistent with this, the inventors found that the absence of LKB1 correlates with increased HIF1-α levels under normoxic conditions, suggesting that this increase in HIF1-α is responsible for increased CCL2. Collectively, these findings demonstrate a novel mechanism for how loss of LKB1 results in metastasis. Thus, the inventors have found that loss of LKB1 results in increased CCL2 secretion through the activation of mTOR, resulting in up-regulation of HIF1-alpha and the subsequent rise in CCL2 transcription, leading to increased monocyte recruitment and metastasis in NSCLC.

CCL2—Table 1

Non-small cell lung cancer (NSCLC) accounts for the majority of cancer related deaths in the US1. Mortality rates for NSCLC have seen little change over the past two decades, with relapse occurring within 5 years in 35-50% of patients. The presence of metastatic disease, both at initial diagnosis and at reoccurrence, is frequent and a primary hurdle to successful treatment. There is a demonstrable need to identity the mechanisms that govern NSCLC metastasis, as this information could provide avenues to develop new treatments for advanced NSCLC. The studies described herein begin to define an innovative mechanism for NSCLC metastasis. Specifically, it will show how the loss of the LKB1 tumor suppressor, the third most mutated gene in NSCLC, promotes metastasis through interactions between LKB1-null NSCLC tumor cells and the immune system. Significant data indicates that interaction between the immune system and tumor cells are involved in metastasis; however how tumor cells initiate this process is poorly understood. Studies indicate an important role for the immune system, in particular macrophages resident within the tumor microenvironment (tumor associated macrophages or TAMs), in tumorigenesis, and metastasis. TAMs are derived from monocytes recruited to the tumor in response to chemotaxic signals secreted by tumor cells, which then differentiate into macrophages within the tumor. Unlike the classical activation or M1 macrophages responsible for defense from infection, TAMs present within tumors are more commonly the M2 phenotype, whose normal functions promote tumor growth and metastasis. Within NSCLC, studies indicate that the presence of M2 TAMs within the tumor microenvironment is associated with metastasis and a poor prognosis. The emerging role for TAMs in NSCLC and other solid tumors has led to strategies targeting TAMs recruitment and function for clinical benefit. The primary strategy has been antibody mediated blockade of the chemokine responsible for monocyte recruitment, CCL2 (C—C motif ligand 2). Expression of CCL2 is increased in NSCLC and other solid tumors and has been found to function in promotion of tumor metastasis. However, CCL2 blockade via antibody mediated binding has had limited efficacy clinically.

The tumor suppressor, LKB1 (Liver Kinase B1) is a serine-threonine kinase that regulates cell growth, metabolism and cell polarity. Mutational inactivation of LKB1 is frequent in sporadic NSCLC, second only to TP5316-21. Current estimates suggest that LKB1 is mutated in at least 30% of NSCLC and more importantly, LKB1 mutation frequently occurs in conjunction with activating mutations in the KRAS oncogene. Studies within transgenic murine models indicate that simultaneous activation of the KRasG12D oncogene and biallelic deletion of LKB1 in the lung not only results in a substantial increase in NSCLC tumor burden, but importantly, results in metastatic disease. Further, work within in vitro model systems and human tumors have substantiated a role for LKB1 in preventing metastasis. Mechanistically, loss of LKB1 results in deregulation of several signaling pathways; however the exact mechanisms responsible for LKB1's inhibitory effects upon metastasis are still being elucidated. The inventors observed that LKB1-null NSCLC cells express and secrete markedly increased levels of CCL2, relative to LKB1 expressing NSCLC cells, which is abrogated by re-expression of LKB1 (Table 1 herein). Based upon observations of increased metastasis with LKB1 loss and the necessary role CCL2 plays in metastasis and tumor growth, this finding of increased CCL2 with LKB1 loss suggest a tangible link between these two observations.

TABLE 1

ELISA of CCL2 levels in LKB1 wt (LKB1+) and LKB1 null (LKB1−) and isogenic H23 LKB1 or kinase dead-LKB1 (KDLKB1) NSCLC cells.

| | CELL LINE | Pg/ml CCL2 |
|---|---|---|
| LKB1+ | H2009 | 34.25, ±2.75 |
| | H358 | 39.75, ±7.75 |
| | H441 | 98.25, ±5.75 |
| LKB1− | H23 | 12866, ±492 |
| | H838 | 3242.5, ±203 |
| | A549 | 3256.75, ±479 |
| | H23 + LKB1 | 63.25, ±1.25 |
| | H23 + KDLKB1 | 7868.25, ±995 |

LKB1 and CCL2—Results

Despite aggressive therapy, mortality rates for Non-small cell lung cancer (NSCLC) have seen little improvement and remains the primary contributor to cancer related mortalities. Several advances have been made towards understanding the molecular and cellular mechanisms that govern NSCLC. In particular has been the appreciation that inactivation of the tumor suppressor, LKB1 is common occurrence in NSCLC, second only to TP53, and occurs in concert with activating KRas mutations. LKB1 regulates cellular growth and polarity and biallelic deletion of LKB1 in several murine transgenic tumor models (including NSCLC) results in a pro-growth and pro-metastatic phenotype. Subsequent genetic analyses indicate that LKB1-null/KRas activated NSCLC tumors represent a distinct genetic subtype of NSCLC and defining the characteristics of these tumors has become an area of considerable importance, as therapies tailored to these tumors could yield substantial clinical benefits for patients with these mutations. In parallel to these studies, has been the improved understanding of the immune system in supporting tumorigenesis. Specifically, activities of tumor associated macrophages (TAMs) are known to contribute to growth and metastasis in several solid tumor types, including NSCLC. It is understood that recruitment of TAMs to the tumor is a consequence of secretion of the chemokine, C—C motif ligand 2 (CCL2), by cancer cells. However the mechanisms that modulate CCL2 expression in tumors remain unclear. The inventors observed that LKB1 loss in NSCLC cells results in increased expression and secretion of C—C motif ligand 2 (CCL2) and increased chemotaxis of the macrophage precursor, monocytes. Based upon the reported effects of LKB1 loss and TAMs in NSCLC growth and metastasis, increased secretion of CCL2 by LKB1-null NSCLC tumors functions to recruit TAMs, which support LKB1-null NSCLC tumor growth and metastasis.

To investigate the effects of LKB1 loss upon NSCLC biology, the inventors re-expressed human LKB1 or an inactive, kinase dead (KD-LKB1) into a LKB1 null lung NSCLC cell line (H23) using a retroviral eukaryotic expression vector and assessed the effects of LKB1 re-expression upon global gene expression. Re-expression of LKB1 in the LKB1 null H23 cell line (H23-LKB1) resulted in considerable changes in expression for several genes, compared to H23 cells expressing KD-LKB1 [H23-KDLKB1]. Of these differentially expressed genes, CCL2 was found to be increased by 242 fold in H23-KDLKB1 compared to H23-LKB1. Consistent with the increase in CCL2 mRNA levels in H23-KDLKB1 cells, a quantitative ELISA assay for CCL2 revealed that H23-KDLKB1 cells secreted 7.8 ng/ml of CCL2, compared to 0.063 ng/ml for H23-LKB1 cells. Further, analysis of a panel of LKB1 null (H23, H838, A549) and LKB1 wild-type (H2009, H358, H441) NSCLC cells showed a comparable phenotype, with LKB1 null NSCLC cells secreting an average of 6.4 ng/ml of CCL2, compared to 0.057 ng/ml for LKB1 wild-type cells (p<0.05). Analysis of CCL2 levels in NSCLC tumors from transgenic KRasG12D/LKB1 wild-type and KRasG12D/LKB1 null mice by immunohistochemistry revealed that KRasG12D/LKB1 null NSCLC tumors displayed markedly high levels of CCL2 staining compared to KRasG12D/LKB1 wild-type NSCLC tumors. Based upon these observations and the known function of CCL2 in recruitment of monocytes, the inventors performed a chemotaxis assay using human peripheral blood mononuclear cells (PBMCs). One million PBMCs were placed in the upper chamber of a 3 uM transwell filter and conditioned media from either H23 (LKB1-null), H2009 (LKB1-wt), or standard media was placed into the bottom chamber. After 1.5 hours, media from the bottom chamber was collected and analyzed by FACs analysis for the presence of monocytes. Exposure to conditioned media from H23 (LKB1-null) NSCLC cells resulted in increased migration of monocytes (circles), compared to conditioned media from H2009 (LKB1-wt) NSCLC cells.

LKB1 Loss Sensitizes Non-Small Cell Lung Cancer Cells to Aggravation of ER Stress Five-year survival rates for non-small cell lung cancer (NSCLC) have seen minimal improvement despite aggressive therapy with standard chemotherapeutic agents, indicating a need for new treatment approaches. Studies show inactivating mutations to the LKB1 tumor suppressor are common in NSCLC and are concurrent with activating mutations to the KRas oncogene. Genetic and mechanistic analyses of KRas/LKB1-null NSCLC tumors suggest these tumors are a phenotypically distinct subpopulation of NSCLC and the unique features of KRas/LKB1-null tumors have potential for therapeutic gain. In the exploration of the mechanism(s) behind increased cytotoxicity of KRas/LKB1-null NSCLC cells to 2-D-Deoxyglucose (2DG), the inventors found that loss of LKB1 in NSCLC cells imparts increased sensitivity to pharmacological aggravation of ER stress. In a panel of NSCLC cell lines, LKB1 expression status correlated to differential expression of the ER stress markers, BiP and CHOP, with 2DG treatment. Treatment of isogenic LKB1-null NSCLC cells ectopically expressing LKB1 or a nonfunctional LKB1 with the ER stress activators, tunicamycin (Tm) or brefeldin A (BFA), revealed that expression of LKB1 increased cell viability and phosphorylation of AMPK. Conversely, isogenic LKB1-null NSCLC cells expressing nonfunctional LKB1 displayed increases in phosphorylation of the ER stress marker, eif2α and markers of ER stress mediated cell death (reactive oxygen species and cleaved caspase-9) following aggravation of ER stress with 2DG, Tm or BFA. The use of 2DG was effective in controlling the growth of KRas/LKB1-null tumors compared to KRas/LKB1-expressing tumors in transgenic NSCLC models and 2DG-treated KRas/LKB1-null NSCLC tumors displayed features consistent with 2DG treatment of in vitro KRas/LKB1-null NSCLC cell lines. Based upon these findings, KRas/LKB1-null NSCLC tumors are more sensitive to pharmacological aggravation of ER stress and this approach could be a treatment for NSCLC patients whose tumors are defined as KRas/LKB1-null.

ER Stress and Regulatory Function of LKB1

Increasing evidence suggests that somatic mutations in the LKB1 tumor suppressor are a common event in the progression of non-small cell lung cancer (NSCLC) and particularly within the lung adenocarcinoma (LA) subtype. LKB1 plays an important role in the regulation of cell metabolism, serving as the primary activator of the metabolic sensor, AMPK. In response to decreases in available ATP, due to nutrient deprivation and/or hypoxia, LKB1-AMPK signaling alters cellular functions in order to restore homeostasis. Loss of LKB1 function and the subsequent failure to activate AMPK during energetic stress conditions, results in cell death. This phenomenon is of clinical importance, as it suggests that induction of energetic stress through pharmacological means might provide significant clinical benefits for LA patients lacking LKB1. The inventors found that pharmacological induction of energetic stress, using the glucose analog, 2-deoxyglucose (2DG), results in increased toxicity in LKB1 null LA cells. Investigating the mechanisms for 2DG-induced toxicity, the inventors found that LKB1 facilitates activation of the Unfolded Protein Response (UPR), a stress response of the Endoplasmic Reticulum. Activity of LKB1 in LA cells correlated with increased activation of the UPR and reduced 2DG-mediated cytotoxicity. Mechanistically, it is shown that LKB1 function is associated with increased activation of ATF6 during ER stress and is necessary for resisting 2DG cytotoxicity. In conclusion, results show a regulatory function of LKB1.

Example 2A

ER Stress

Lung cancer, and more specifically non-small cell lung cancer (NSCLC), contributes significantly to cancer related mortalities within the United States. The histological subtype adenocarcinoma accounts for the majority of the deaths from NSCLC. Morphologically distinct from other NSCLC subtypes, studies have also shown differences between NSCLC histological subtypes at the molecular level. Mutational analyses of both the K-Ras and EGFR oncogenes have demonstrated stark differences in mutational frequencies of these genes between NSCLC histological subtypes. Likewise, analyses of the tumor suppressor gene, LKB1, have found inactivating mutations at a much higher frequency in adenocarcinomas compared to other NSCLC subtypes (34%-adenocarcinoma, 19%-squamous cell carcinoma, 14%-large cell carcinoma), indicating that inactivation of LKB1 in lung adenocarcinoma is critical to progression of the disease. Yet, while data has elucidated the functional contributions of oncogenic activation of K-Ras and EGFR to lung adenocarcinoma, there is little understanding of the role LKB1 has in lung adenocarcinoma.

LKB1 is a critical regulator of cell metabolism, modulating activity of 5'-adenosine mono-phosphate activated protein kinase (AMPK). Depletion of cellular ATP levels, due to hypoxia and/or nutrient deprivation, results in LKB1 dependent phosphorylation and activation of AMPK. Once activated, LKB1-AMPK signaling interacts with a variety of proteins, altering cell metabolism and inhibiting cell growth, in order to maintain cell homeostasis and survival. Considerable data has demonstrated the necessity of LKB1 in these functions. Reduction of cellular ATP, either by pharmacological or environmental conditions, induces cell death in cells lacking the LKB1 gene. Paradoxically, inactivation of LKB1 and LKB1-AMPK signaling removes a significant check upon cell growth, a necessary step in cancer progression. Thus, while loss of LKB1 may provide a growth advantage to lung adenocarcinoma cells, the lack of LKB1 may also require significant alterations in metabolic functions in order to survive.

One of the most basic requirements of all cells is the synthesis of new proteins. Within eukaryotes, the majority of protein synthesis is tasked to the Endoplasmic Reticulum (ER), which mediates folding and post-translational modifications within its lumen. Due to the critical function the ER plays in normal cellular homeostasis, ER function is tightly regulated. Stimuli, such as nutrient deprivation and hypoxia, disrupt normal ER function and lead to increases in unfolded/misfolded proteins within the lumen of the ER. This condition, termed ER stress, represents a severe threat to the health of both the ER and the cell. Thus, eukaryotic cells have evolved a highly conserved process, the unfolded protein response (UPR), to protect both the ER and the cell. Activation of the UPR occurs through three distinct ER stress transducers, PKR-like endoplasmic reticulum kinase (PERK), inositol-requiring and endonuclease gene 1 (IRE1), and activating transcription factor-6 (ATF6), which initiate actions that result in transient inhibition of global protein translation, while allowing the specific expression and translation of target proteins which function to reduce misfolded/unfolded protein levels within the ER through protein folding and degradation. While it is still not completely understood how PERK, IRE1 and ATF6 function to adapt the cell and ER via the UPR, it is clear that activation of the three arms of the UPR (PERK, IRE1 and ATF6) are necessary for cell survival. Inhibition or disruption either of PERK, IRE1 or ATF6 severely impairs cell survival during ER stress, while constitutive activation either of PERK, IRE1 or ATF6 promote cell survival during conditions of prolonged or extreme ER stress. These observations have led to investigations of UPR function within disease, with evidence supportive of a role for the UPR in diabetes and cancer.

ER Stress and Regulatory Function of LKB1—Materials and Methods

Cell Culture and Reagents

H23, H2126, H838, H1395, H2009, H358, H1975 and H441 lung adenocarcinoma cell lines were obtained from ATCC and maintained in RPMI 1640 (Invitrogen) under standard tissue culture conditions. Antibodies to phosphorylated AMPK, AMPK, phosphorylated S6, S6, GRP78/BiP, CHOP, cleaved human PARP, Lamin A/C were all purchased from Cell Signaling Technologies. The rabbit polyclonal antibody specific to the aminoterminal end of ATF6 was purchased from Abcam (# ab65838). 2-Deoxyglucose (2DG, Sigma) was diluted to a 1M stock in sterile phosphate buffered saline. Compound C, tunicamycin, bortezomib and celecoxib were purchased from Tocris Bioscience (MS, USA) and diluted in DMSO. The pBabe retroviral constructs containing FLAG tagged full length LKB1 and the kinase dead LKB1 (KDLKB1) originated in Dr. Lewis Cantley's laboratory (Harvard Medical School, MA) and the constitutively active HA tagged ATF6 (caATF6) originated in the laboratory of Ron Prywes (Columbia University, NY) and all plasmids were obtained from Addgene.org (Cambridge, Mass.). The isogenic H23-KDLKB1 and H23-LKB1 have been described previously.

Small Interfering RNA Knockdown of LKB1, PERK, IRE1 and ATF6

SMARTpool siRNAs against human LKB1, PERK, IRE1 and ATF6 were purchased from Thermo Scientific/Dharmacon and diluted according to manufacturer's instructions. Transfections with siRNA oligomers were performed as described previously. 48 hours following transfection, cells were treated with 20 mM 2DG and lysed for immunoblotting as described below or plated for clonogenic assays.

Transfection and Retroviral Infection

Retroviral packaging of KDLKB1 (DN-LKB1), infection and puromycin selection of H2009 and H358 was performed as described previously. Transfection of caATF6 or empty vector into H838 and H23 LA cells was performed using Polyfect (Qiagen) according to manufacturer's instructions. Twenty-four hours following transfection, cells were plated for clonogenic assays and used for isolation of total protein lysates.

Clonogenic Assay

Clonogenic survival assay were performed in 6 well dishes. Briefly, 300-500 cells were plated per well and allowed to attach overnight. Drugs were diluted fresh into media and cells were treated for 24 hours. Drug containing media was removed and replaced with fresh media. After 14 days, cells were fixed in 10% Methanol/10% Acetic Acid and stained with 0.5% crystal violet. After washing in ddH$_2$O, plates were allowed to dry and colonies of 50 cells or more were counted. The surviving fraction was calculated according to methods described by Franken, et al.

Cell Lysis and Immunoblotting

Cells were incubated on ice for 30 minutes with a lysis buffer containing 10 mM Tris-HCL, 150 mM NaCl, 0.1% SDS and 1% IGEPAL (Sigma). Immediately before use, a protease inhibitor cocktail (Sigma) and two phosphatase cocktails I and II (Sigma) were added to the lysis buffer. Lysates were transferred to tubes and insoluble material was pelleted by centrifugation. Nuclear protein fractions were isolated using a NE-PER protein extraction kit (Thermo-Fisher) according to manufacturer's instructions. Protein concentration was determined using the Bio-Rad DC protein kit. For immunoblotting, 50-100 ug of total protein lysates was separated by SDS-PAGE and transferred to nitrocellulose. Blots were blocked in 5% milk/Tris buffered saline/

0.1% TWEEN® 20 (polyoxyethylenesorbitan monolaurate) (TBST) and primary antibodies were diluted in 5% Bovine Serum Albumin (Sigma)/TBST and incubated overnight at 4° C. Blots were developed with ECL plus (GE) and visualized on a Kodak Image station.

ERSE Reporter Assay

For analysis of ER stress induced transcription, cells were plated onto 96 well plates at a density of 5000 cell/well and allowed to attach. The premixed ERSE luciferase and Renilla constructs were purchased from SA Bioscience and transfected with Lipofectatmine 2000 (Invitrogen) according to manufacturer's instructions. Following treatment for six hours, luciferase and renilla levels were analyzed using the Dual-GLO luciferase assay system and relative light units (RLU) were determined on a Beckman Coluter DTX880. To generate fold induction, luciferase RLUs were normalized to renilla RLUs.

Quantitative Reverse Transcription-PCR (qRT-PCR) Analysis of HERPUD1 and XBP1 mRNAs mRNAs were isolated from ~70% confluent 60 mm cell culture dishes following appropriate treatment times using the Qiagen RNeasy Mini Kit (Qiagen Inc. —USA, Valencia, Calif.). Quality and quantity of isolated mRNAs were assessed using the NanoDrop ND-1000 spectrophotometer (Thermo Scientific, Wilmington, Del.). cDNAs were synthesized using 750 ng of total RNA following the SuperScript III First-Strand Synthesis SuperMix (Life Technologies, Carlsbad, Calif.) according to manufacturer's instructions. PCR analyses of mRNAs were carried out using gene specific primers (Invitrogen) in triplicate in a 384-well plate using a LightCycler 480 (Roche Applied Sciences, Indianapolis, Ind.) with LightCycler 480 SYBR Green I Master (Roche Applied Sciences) fluorescence signal detection after each cycle of amplification. Normalized crossing points of mRNA versus GAPDH were used to calculate relative fold up-/down-regulation by the delta-delta Ct method.

XBP-1 Detection

For identification of processed and unprocessed XBP-1, total RNA was isolated from treated cells using the Qiagen RNeasy Mini Kit (Qiagen Inc., USA, Valencia, Calif.) according to manufacturer's specifications. 1 ug of total RNA was used in an RT-PCR reaction using the SuperScript III One-Step RT-PCR System and primers to XBP-1 (anti-sense-TCCTTCTGGGTAGACCTCTGGGAG (SEQ ID NO:1), sense-AAACAGAGTAGCAGCTCAGACTGC (SEQ ID NO:2)). Spliced and unspliced XBP-1 fragments were separated by 3% agarose gel and stained with ethidium bromide. Gels were visualized and photographed on a Kodak Gel imager. For a loading control, RT-PCR of β-actin was performed.

Caspase 3/7 Activity Assay

H23-LKB1 and H23-KDLKB1 cell were plated as described previously and treated for 24 hours with tunicamycin (5 ug/ml) or vehicle (DMSO). Activity of Caspases 3 and 7 were determined using a Promega Caspase-Glo 3/7 kit and data analyzed as described previously.

Microarray Analysis

Microarray analysis of H23 and H2009 cells was performed as described previously. UPR target genes were identified from the statistically significant (Student t test, $p<0.05$) gene lists of genes with at least a 2-fold change in expression relative to untreated control. UPR function of identified genes was determined by searching within PubMed and Genebank databases.

ER Stress and Regulatory Function of LKB1—Results

UPR Activation is Necessary for Survival to 2DG in LKB1 Expressing LA Cells and Correlates with LKB1-AMPK Signaling 2-deoxy-D-glucose (2DG), a non-hydrolyzable analog of glucose, has considerable therapeutic activity in several tumor types and has attracted attention as a possible chemotherapeutic. Previously, it was found that the tumor suppressor LKB1 significantly reduces the cytotoxicity of 2DG in lung adenocarcinoma (LA) cells and lack of LKB1 activity sensitized LA cells to 2DG's cytotoxic effects. Cytotoxicity of 2DG has been linked to disruption of protein translation (via inhibition of protein glycosylation) and induction of ER stress. Evidence indicates that initiation of the UPR (via activation of PERK, IRE1 and ATF6) serves to reduce ER stress and promote cell survival. Based upon the observations of 2DG cytotoxicity due to ER stress and the role of the UPR, the inventors believed that activation of the UPR may be responsible for reduced 2DG cytotoxicity in LKB1 expressing LA cells. The inventors used H2009 LA cells, a cell line wild-type for LKB1 and resistant to 2DG. H2009 LA cells were depleted of PERK, IRE1, ATF6 or LKB1 expression by siRNA knockdown and effects upon 2DG cytotoxicity were evaluated in clonogenic survival assays. As expected, knockdown of LKB1 sensitized H2009 to 2DG treatment, particularly at low doses of 2DG. Likewise, depletion of the three UPR activators (PERK, IRE1, ATF6) sensitized H2009 cells to 2DG across all concentrations, suggesting a dependence upon the UPR for survival in H2009 cells in response to 2DG. Based upon these findings, the inventors examined the protein levels of BiP/GRP78 (glucose response protein 78) and CHOP/GADD153 (C/EBP homologous protein), two proteins critical in mediating the UPR and whose increased expression are a common indicator of ER stress and the UPR, in H2009 cells and the LA cell line, H23, which lacks LKB1 expression due genetic mutation. Consistent with previous studies, the presence of LKB1 in H2009 cells resulted in phosphorylation and activation of AMPK with 2DG treatment, a phenotype absent from LKB1 null H23 cells. Interestingly, analysis of CHOP and BiP protein levels revealed significantly increased expression of these two UPR targets within H2009 cells, compared to H23 cells. The inventors expanded their analysis to additional LKB1 expressing (H358, H1975, H441) and LKB1 null (H2126, H838, H1395) LA cell lines in order to determine if this phenotype was restricted to the H2009 and H23 cell lines. Consistent with findings in H2009 and H23 cells, the presence of LKB1 resulted in activation of AMPK and increased expression of CHOP and BiP with 2DG treatment, which was not observed in LA cells lacking LKB1 treated with 2DG. It was shown that 2DG activated apoptosis in LKB1 null LA cells and the presence of LKB1 reduced this cytotoxic effect of 2DG. Analysis of apoptosis in the LA cell panel revealed that 2DG treatment resulted in increased cleavage of poly(ADP-ribose) polymerase (PARP) in LKB1 null LA cells. PARP cleavage was markedly decreased in LKB1 wild-type LA cells, correlating with increased expression of CHOP and BiP.

LKB1-AMPK Signaling Facilitates Expression of CHOP and BiP in Response to 2DG

In order to investigate whether LKB1 is necessary for increased expression of CHOP and BiP in response to 2DG treatment, the inventors analyzed CHOP and BiP protein expression in isogenic LA cell lines. Stable expression of a functional, full length LKB1 in H23 cells (H23-LKB1) restores LKB1-AMPK signaling and reduces the cytotoxic effect of 2DG, while introduction of an inactive, kinase dead LKB1 (H23-KDLKB1) fails to activate AMPK with 2DG treatment and 2DG cytotoxicity present in the parental H23 cell line. Re-expression of LKB1, but not KDLKB1 within the H23-LKB1 cell line restored expression of both CHOP and BiP in response to 2DG treatment in a time dependent manner, comparable to the observations in the other LA cell lines. To confirm these findings, the inventors depleted LKB1 with siRNA in H2009 cells and H358 LA cell lines. Knockdown of LKB1 resulted in decreased activation of AMPK, as well as reduced expression of CHOP and BiP when treated with 2DG, further indicating that LKB1 is necessary in facilitating the expression of CHOP and BiP during 2DG induced ER stress. The inventors next investigated whether AMPK was necessary in facilitating expression of CHOP and BiP during 2DG ER stress, using the kinase dead LKB1 in a dominant negative fashion to decrease AMPK activity, an approach that has been used previously. Stable expression of the kinase dead/dominant negative LKB1 (DN-LKB1) in H358 and H2009 reduced AMPK activation with exposure to 2DG compared to H358 and H2009 cells carrying the empty pBABE vector. Treatment of H2009 cells expressing DN-LKB1 also displayed CHOP and BiP protein levels, while H358-DN-LKB1 cells showed reduced levels of BiP in a time dependent manner when treated with 2DG. Further, pharmacological inhibition of AMPK with compound C, a known AMPK inhibitor, prevented expression of both BiP and CHOP. Taken together, these data indicate that LKB1-AMPK signaling is necessary to facilitate expression of CHOP and BiP in response to 2DG induced ER stress.

Loss of LKB1 Alters the UPR Activator ATF6 Upon 2DG Induction of ER Stress

Considerable evidence indicates that failure to properly activate any of the three arms of the UPR severely impairs the ability of cells to survive ER stress. Since it was observed that LKB1 activity increased expression of CHOP and BiP in response to 2DG, the inventors investigated whether LKB1 had any effect upon the three UPR activators, PERK, IRE1 and ATF6. Within the ER, increases in misfolded/unfolded proteins activate PERK and IRE1. PERK is a kinase, phosphorylating the eukaryotic translation initiation factor 2 (eif2α), while ER stress activates IRE1's endoribonuclease domain that cleaves a 26-bp intron within the mRNA transcript of XBP1 (X-box binding protein-1). Removal of the 26-bp intron permits translation of the XBP1 mRNA, which encodes a potent transcription factor. Measurement of eif2α phosphorylation and XBP1 splicing are common indicators of both PERK and IRE1 activity, as well as UPR activation. Re-expression of LKB1 in LKB1 null H23 LA cells, had no effect upon levels of PERK mediated phosphorylation of eif2α (top panel) nor the amount of cleaved XBP1 mRNA (bottom panel) in response to 2DG. The inventors observed no differences in eif2α phosphorylation or XBP1 splicing in parental LKB1 null H23 and LKB1 wild-type H2009 LA cells treated with 2DG. Taken together, these findings suggest LKB1 has no effect upon PERK or IRE1 function. The inventors next analyzed ATF6 activation in H23-LKB1 and H23-KDLKB1 LA cells treated with 2DG. ATF6 is synthesized as an inactive precursor transmembrane protein, residing within the ER membrane. Stimulation by unfolded/misfolded proteins of the stress-sensing ER luminal domain induces proteolytic cleavage of ATF6, releasing its cytosolic domain. The cytosolic domain of ATF6 then translocates to the nucleus, where it functions as a potent activator of UPR target gene expression. To investigate whether LKB1 had any impact upon ATF6 activation, the inventors performed immunoblot analysis of ATF6 in H23-LKB1 and H23-KDLKB1 LA cells treated with 2DG. Immunoblot analysis revealed the low amounts of active (cleaved) ATF6 in both H23-LKB1 and H23-KDLKB1 without 2DG treatment, consistent with previous reports of ATF6 activation in tumor cells. Treatment with 2DG increased formation of active (cleaved) ATF6 in H23-LKB1. However, 2DG treatment resulted in a significant decrease in active ATF6 in H23-KDLKB1 cells. The inventors next evaluated levels of active ATF6 within nuclear protein fractions from H23-LKB1 and H23-KDLKB1 LA cells treated with 2DG. Immunoblot analysis revealed increased ATF6 within the nuclear protein fraction of H23-LKB1 cells, but not H23-KDLKB1. Further treatment of H23-LKB1 and H23-KDLKB1 with tunicamycin, a known activator of ER stress and the UPR, had comparable results, confirming that lack of LKB1 function results in deregulation of ATF6 activation upon induction of ER stress.

LKB1 Facilitates UPR Target Gene Expression

ATF6 is necessary for adaptation of the ER to chronic stress, regulating the expression of ER quality control genes, which function in protein folding, secretion and degradation. Because ATF6 activation is increased in LKB1 expressing LA cells, they examined whether the transcription of UPR target genes are upregulated. UPR transcriptional genes share a unique transcriptional response element (ER stress response element or ERSE) which ATF6 binds to drive gene expression. The inventors transiently transfected a luciferase reporter plasmid, in which expression of luciferase is driven by the consensus ERSE (CCAAT (N9) CCACG), into H23-LKB1 and H23-KDLKB1 LA cells. Following 6 hours of treatment with 2DG, re-expression of LKB1 in the LKB1 null H23 LA cells significantly increased the activity of the ERSE luciferase reporter, compared to expression of a kinase dead LKB1. Further, untreated H23-LKB1 and H23-KDLKB1 cells also showed increased activity of the ERSE reporter, consistent with observations of increased UPR activity within tumor cells. Previously, they performed microarray-based gene expression analysis on H2009 and H23 LA cells treated with 2DG, which were reanalyzed for known UPR target genes. Consistent with the increase in UPR target gene reporter activity in LKB1 expressing cells, the inventors identified a number of ATF6 target genes within the statistically significant gene lists that were considerably increased in LKB1 expressing H2009 LA cells, compared to LKB1 null H23 cells. The inventors chose two genes from this list (HERPUD1, XBP1) and analyzed their expression by qPCR within H23-LKB1 and H23-KDLKB1 LA cells treated with 2DG, in order to further investigate whether LKB1 was facilitating the expression of ATF6 target genes. H23-LKB1 cells had significantly increased expression levels of both ATF6 target genes, compared to H23-KDLKB1 LA cells. To confirm these findings, the inventors treated H23-LKB1 and H23-KDLKB1 LA cells with tunicamycin and performed qPCR for both HERPUD1 and XBP1. Consistent with our observations with 2DG treatment, both HERPUD1 and XBP1 expression were significantly increased in H23-LKB1 cells, relative to H23-KDLKB1 cells. In order to determine if the loss of ATF6 UPR gene transcription is responsible for increased 2DG cytotoxicity in LKB1 null LA cells, the inventors transiently overexpressed active ATF6 (caATF6) in the LKB1 null LA cell lines, H23 and H838 and assessed the effects upon 2DG cytotoxicity. Overexpression of caATF6 significantly improved the survival of H838 and H23 across all doses of 2DG, compared to H23 and H838 LA cells transfected with empty vector. Collectively, these findings suggest that loss of LKB1 activity in LA cells results in reduced ATF6 activation during ER stress conditions. The subsequent loss of ATF6 mediated gene transcription compromises ER function, leading to cell death.

Lack of LKB1 and Insufficient UPR Activation is not Exclusive to 2DG

The inventors examined whether LKB1 null LA cells may also display increased cytotoxicity to other pharmacological activators of ER stress. The inventors initially treated H23-LKB1 and H23-KDLKB1 with tunicamycin and assessed UPR activation. Consistent with 2DG treatment, tunicamycin treatment resulted in increased expression of BiP and CHOP only in H23-LKB1 LA cells, but not in H23-KDLKB1. Further, tunicamycin displayed increased cytotoxicity and apoptosis in H23-KDLKB1 cells compared to H23-LKB1 cells. The Cox-2 inhibitor, celecoxib and the dipeptide boronic acid proteasome inhibitor, bortezomib are both known to induce ER stress within tumor cells. Treatment of H23-LKB1 and H23-KDLKB1 with celecoxib or bortezomib resulted in increased UPR activation only in H23-LKB1 cells, as well as decreased cytotoxicity compared to H23-KDLKB1 LA cells. Taken together, LKB1 facilitates UPR target gene transcription to promote survival during ER stress. Lack of LKB1 in LA cells results in decreased UPR target gene transcription, resulting in cell death, indicating a possible avenue for treatment of LA.

Example 2B

Materials and Methods
Cell Culture and Reagents

A427, H23, H2126, H838, H1395, H2009, H358, H1975 and H441 NSCLC cell lines were obtained from ATCC and maintained in RPMI 1640 (Invitrogen) under standard tissue culture conditions. Antibodies to phosphorylated AMPK, AMPK, LKB1, GRP78/BiP, CHOP, cleaved PARP, cleaved Caspase 9, phosphorylated eif2a, eif2a were all purchased from Cell Signaling Technologies. 2-D-Deoxyglucose (2DG, Sigma) was diluted to a 1M stock in sterile phosphate buffered saline. Tunicamycin (Tm), brefeldin-A (BFA), celecoxib and bortezomib were purchased from Tocris Bioscience (MS, USA) and diluted in DMSO. The pBabe retroviral constructs containing FLAG-tagged full length LKB1 and the kinase dead LKB1 (KDLKB1) originated in Dr. Lewis Cantley's laboratory (Harvard Medical School, MA) and were obtained from Addgene.org (Cambridge, Mass.). The isogenic H23-KDLKB1, H23-LKB1, A427-LKB1, A427-KDLKB1, H838-LKB1 and H838-KDLKB1 cell lines were derived using methods described previously [Inge et al., *Expression of LKB1 tumor suppressor in non-small cell lung cancer determines sensitivity to 2-deoxyglucose*, J. THOR. CARDIOVAS. SURG. (2008)]. CellROX™ Green reagent was purchased from Life Technologies. Cyclohexamide (CHX) was purchased from Selleck and diluted in DMSO.

Cell Lysis and Immunoblotting

Cells were washed once with ice-cold PBS and incubated on ice for 30 min with a lysis buffer containing 10 mM Tris-HCl, 150 mM NaCl, 0.1% SDS and 1% IGEPAL (Sigma) to which a protease inhibitor cocktail (Sigma) and two phosphatase cocktails I and II (Sigma) were added immediately before use. Lysates were transferred to tubes and insoluble material was pelleted by centrifugation. For immunoblotting, 50-100 μg of total protein lysates were separated by SDS-PAGE and transferred to nitrocellulose. Blots were blocked in 5% milk/Tris buffered saline/0.1% TWEEN® 20 (polyoxyethylenesorbitan monolaurate) (TBST) and primary antibodies were diluted in 5% Bovine Serum Albumin (Sigma)/TBST and incubated overnight at 4° C. Blots were developed with ECL plus (GE) and visualized on a Kodak Image station.

ATP Measurement/Cell Viability

500 H838 or A427 cells stably expressing either LKB1 or KDLKB1 were plated in 96 well plates. The following day, cells were dosed with the indicated treatments for 48 h. Cellular ATP levels were assessed using the CellTiter-Glo Luminescent Cell Viability Assay substrate (Promega) according to manufacturer's instructions. Luminescence was read using the DTX 880 Multimode Detector. Cellular ATP/cell viability was calculated relative to vehicle treated control.

Flow Cytometry of ROS Levels

To analyze levels of reactive oxygen species (ROS), $1 \times 10^6$ H838-KDLKB1 and H838-LKB1 cells were plated and treated with the indicated drugs. Cells were then stained with 0.5 1M CellRox™ for 30 min at 37° C., collected by trypsinization and washed with PBS. Following fixation with 2% Paraformaldehyde/PBS for 20 min, cells were brought to a final volume of 500 ll in PBS. CellRox™ staining of ROS was assessed using the Accuri C6 Flow Cytometer (BD Biosciences, San Jose, Calif., USA) with the threshold set at 80,000. A total of 30,000 events were collected per sample and ROS staining intensity determined using FCS Express 4 Flow Cytometer software. Background events were gated out using unstained control. Histogram plots were overlaid and histogram subtraction was performed by subtracting the integral of the stained control from the treated sample.

Figure 2:
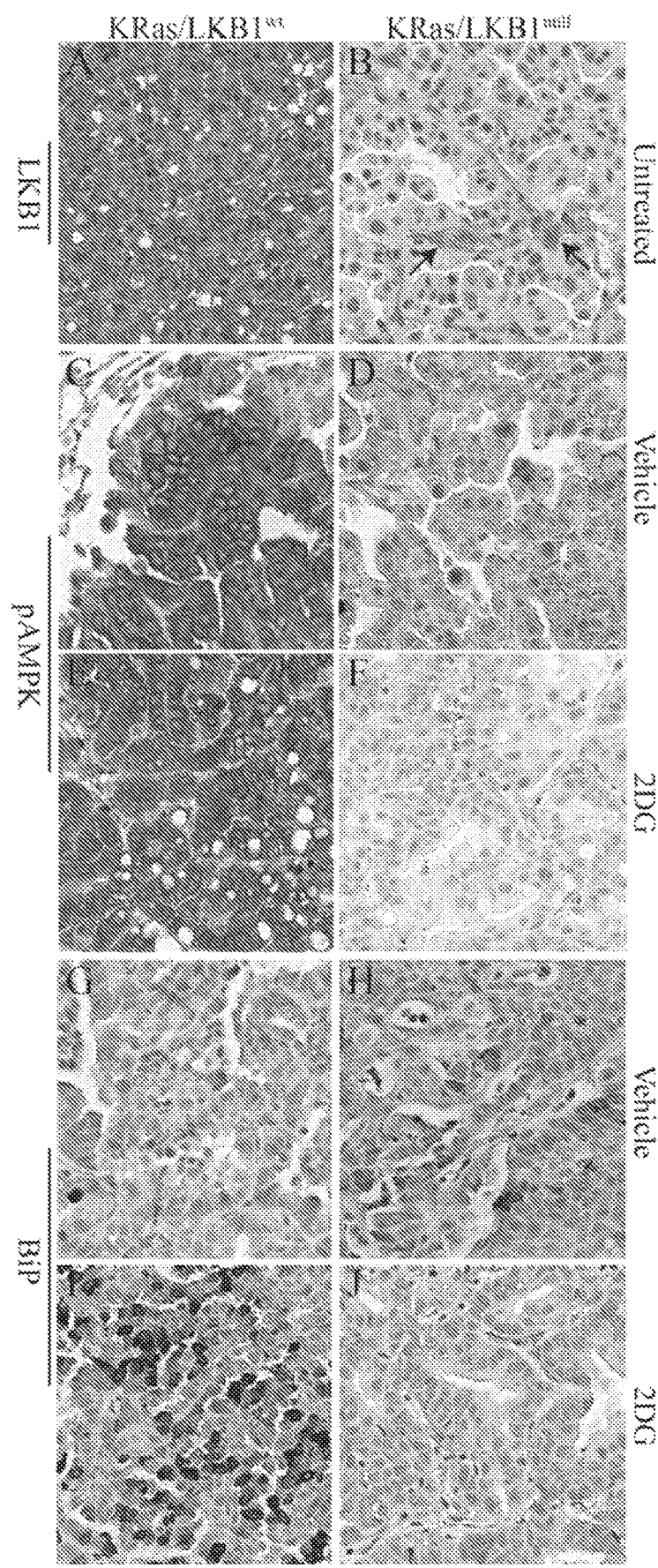
FIG. 2 shows, in accordance with embodiments herein, immunohistochemical staining of KRas/LKB1$^{wt}$ and KRas/LKB1$^{null}$ NSCLC tumors. (A and B) LKB1 staining of KRas/LKB1$^{wt}$ and KRas/LKB1$^{null}$ NSCLC tumors. Arrows (B) indicate LKB1 positive stromal cells. (C-F) Phosphorylated AMPK$^{thr172}$ (pAMPK) staining in KRas/LKB1$^{wt}$ and KRas/LKB1$^{null}$ NSCLC, treated with vehicle (C and D) or 2DG (E and F) for two days (500 mg/kg, BID). (G-J) BiP/GRP78 staining in KRas/LKB1$^{wt}$ and KRas/LKB1$^{null}$ NSCLC, treated with vehicle (G, H) or 2DG (I, J) for two days (500 mg/kg, BID). Magnification=20×.

Murine Transgenic Models of KRas and KRas/LKB1 Null NSCLC $KRas^{G12D}/LKB1^{lox/lox}$ ($KRas/LKB1^{null}$) were generated by selective breeding of Lox-Stop-Lox $KRas^{G12D}$ mice, purchased from Jackson Laboratories (Bar-Harbor, Me.), with $LKB1^{lox/lox}$ mice obtained from Mouse Repository at the NCI and were inbred on a FVB background. $KRas^{G12D}/LKB1^{wt/wt}$ ($KRas/LKB1^{wt}$) mice were generated by back-crossing Lox-Stop-Lox $KRas^{G12D}$ onto a FVB background. Induction of lung tumors was performed. Briefly, six-week-old $KRas/LKB1^{null}$ and $KRas/LKB1^{wt}$ mice were transiently infected with $5 \times 10^6$ p.f.u. of Cre adenovirus (University of Iowa adenoviral core) via intranasal infection. At ~6 weeks ($KRas/LKB1^{null}$) or ~10 weeks ($KRas/LKB1^{wt}$) post-infection, mice underwent a baseline MRI scan to determine the baseline tumor burden. Mice with identified disease were randomized for daily treatment with either vehicle (PBS) or 500 mg/kg 2DG for three weeks, at which time mice received a follow-up MRI scan, sacrificed and the presence of disease confirmed by gross assessment and histology. For data generated in FIG. 2, $KRas/LKB1^{null}$ and $KRas/LKB1^{wt}$ mice with MRI positive tumors were treated either with 2DG (500 mg/kg) or vehicle (PBS) twice a day for two days before sacrifice and necropsy of tumor tissue. Mice received daily checks to monitor for clinical signs of disease (labored breathing, weight loss) and all procedures were under a protocol approved by the St. Joseph's Hospital and Medical Center IACUC committee.

MRI Imaging

All the scans were performed using a 7T small animal, 30-cm horizontal-bore magnet and BioSpec Advance III spectrometer (Bruker, Billerica, Mass.) with a 72 mm quadrature volume coil. Each animal was induced and maintained under isoflurane anesthesia, 3.0% and 1.5%, respectively, and delivered with 1.5 L/min of 100% oxygen. During MRI scans, the animal's respiration was continually monitored by a small animal monitoring and gating system (SA Instruments, Stoney Brook, N.Y.) via a pillow sensor positioned on top of the abdomen. Mice were placed on a heated animal bed system (Bruker, Billerica, Mass.) and the normal body temperature (36-37° C.) was maintained. For MR imaging, a Fast Low Angle Shot (FLASH) sequence (TR/TE=40 ms/2 ms; FOV=60 mm×60 mm; Average=2; matrix=256×256; Flip Angle=30°) was used to acquire initial scout images, which were used for locating the lung region for subsequent images. Then T1 weighted images were obtained with the Fast Imaging with Steady State Precession (FISP) sequence (TR/TE 5.262 ms/2.0 ms; 8 segments; FOV=30 mm×30 mm; matrix=256×256; slice thickness=1.0 mm; Flip angle, 20°; 22 averages; total acquisition time=17 min). During the scan, motion artifacts were suppressed with multiple averages and respiration triggering. The images were saved in analyze format, and the further image processing and tumor volume measurements were performed with ImageJ (National Institutes of Health, Bethesda, Md., USA), using 17 sequential image scans. Change in tumor volumes was determined by comparison of baseline tumor volume to tumor volume following three weeks of treatment.

Clonogenic Assay

Clonogenic survival assay were performed in 6 well dishes. Briefly, 200 of indicated cells were plated per well and allowed to attach overnight. Were indicated cells were pre-treated with 125 ng/ml of cyclohexamide (CHX) for one hour. Indicated drugs were diluted fresh into media and cells were treated for 24 h, at which time the drug containing media was removed and replaced with fresh media. After 14 days, cells were fixed in 10% Methanol/10% Acetic Acid and stained with 0.5% crystal violet. After washing in ddH$_2$O, plates were allowed to dry and colonies of 50 cells or more were counted. The surviving fraction was calculated according to methods described by Franken et al. [*Clonogenic assay of cells in vitro*, NAT. PROT. 1 (5) (2006) 2315-2319].

Immunohistochemical Staining

Lungs from either KRas/LKB1$^{null}$ or KRas/LKB1$^{wt}$ mice with identified tumor and treated with 2DG (500 mg/kg, two doses over a 24 h period) were fixed overnight in 10% neutral buffered formalin and paraffin embedded using routine procedures. FFPE samples of KRas/LKB1$^{null}$ and KRas/LKB1$^{wt}$ NSCLC tumors were sectioned using standard procedures and adhered to charged microscope slides. Five μM sections underwent heat induced epitope retrieval and immunohistochemical (IHC) staining of tissue was performed. Antibodies to pAMPK, LKB1 and BiP were purchased from Cell Signaling. Slides were scanned using the Aperio system (Leica Biosystems, Buffalo Grove, Ill.) and images collected at a magnification of 20×.

Results

2DG Displays Improved Pre-Clinical Efficacy In Vivo Using a Transgenic Model of KRas/LKB1-Deficient NSCLC 2-deoxy-D-glucose (2DG), a non-hydrolyzable analog of glucose, has therapeutic activity in several tumor types and has attracted attention as a possible chemotherapeutic. We found that lack of LKB1 activity sensitized NSCLC cells to 2DG-mediated cytotoxicity in vitro. Based upon these findings, we assessed the role of LKB1 in modulating the effects of 2DG in NSCLC in vivo using two well-characterized transgenic models of NSCLC (KRas/LKB1$^{wt}$ and KRas/LKB1$^{null}$). KRas/LKB1$^{wt}$ and KRas/LKB1$^{null}$ mice underwent an MRI scan to determine baseline tumor burden at either 10 weeks (KRas/LKB1$^{wt}$) or 6 weeks (KRas/LKB1$^{null}$) postinfection with adeno-Cre (FIG. 1A). Animals with identified tumor were randomized for treatment with vehicle (PBS) or 2DG at 500 mg/kg, a dose shown to have limited efficacy in vivo and re-imaged after three weeks of treatment to determine the change in tumor volume. Treatment with 2DG reduced the growth of NSCLC tumors in both KRas/LKB1 wt and KRas/LKB1$^{null}$ mice, compared to vehicle (FIGS. 1A and B) after three weeks of treatment.

However, KRas/LKB1$^{null}$ tumors displayed a statistically greater response to 2DG (p=0.0032), compared to KRas/LKB1$^{wt}$ tumors (FIG. 1B). Despite reducing the growth of NSCLC tumors, we did not observe any effects upon metastasis (a reported feature of the KRas/LKB1$^{null}$ model) under gross assessment at necropsy in KRas/LKB1$^{null}$ mice with 2DG treatment (data not shown).

2DG Induction of BiP/GRP78 is LKB1 Dependent

We next investigated the effects of 2DG treatment in KRas/LKB1$^{wt}$ and KRas/LKB1$^{null}$ mice by performing IHC staining for phosphorylated AMPK (pAMPK) and glucose response protein 78 (HSPA5/GRP78) or BiP, a protein shown to be up-regulated in KRas/LKB1$^{wt}$ and KRas/LKB1$^{null}$ NSCLC tumors in response to metabolic stress. Tumors from KRas/LKB1$^{wt}$ and KRas/LKB1$^{null}$ mice were also stained for LKB1 to confirm Cre-mediated deletion of the LKB1 gene. LKB1 (FIG. 2B) and pAMPK (FIGS. 2D and F) were absent from KRas/LKB1$^{null}$ tumors, while staining of both LKB1 (FIG. 2A) and pAMPK (FIGS. 2C and E) were observable in NSCLC tumors from KRas/LKB1$^{wt}$ mice. IHC staining of BiP revealed that treatment with 2DG resulted in a significant increase in BiP protein levels in NSCLC tumor cells of KRas/LKB1$^{wt}$ mice (FIGS. 2G and I), but not in tumors from KRas/LKB1$^{null}$ mice (FIGS. 2H and J).

Figure 3:
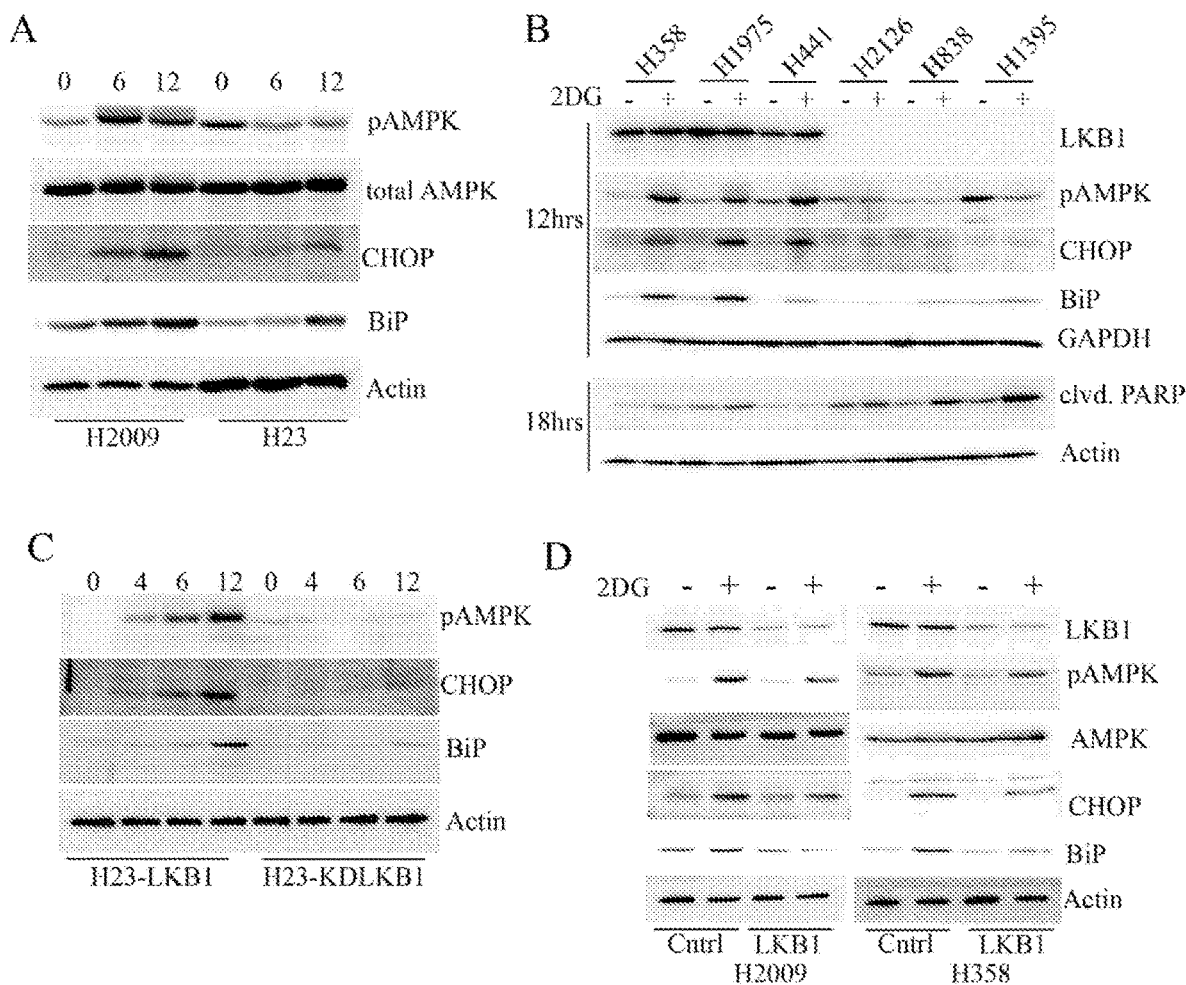
FIG. 3 shows, in accordance with embodiments herein, 2DG induced ER stress is altered in LKB1-deficient NSCLC cells. (A) LKB1 signaling correlates with expression of ER stress markers. LKB1 expressing H2009 or LKB1 null H23 LA cells were treated with 20 mM 2DG for the indicated times. Following SDS-PAGE, samples were immunoblotted for LKB1, phosphorylated AMPK and CHOP and BiP, markers of ER stress and the UPR. Actin and total AMPK were used as loading controls. Blot is representative of 4 independent experiments. (B) LKB1 expression correlates with expression of ER stress markers and decreased apoptosis in LA cells. A panel of LA cells (H358, H1975, H441-LKB1+; H2126, H838, H1395-LKB1−) was treated for 12 and 18 h with 20 mM 2DG. Total protein lysates were immunoblotted with antibodies specific to LKB1, CHOP, BiP, phosphorylated AMPK and cleaved PARP. Actin was used as a loading control. Blot is representative of three independent experiments. (C) Re-expression of LKB1 in LKB1 null H23 LA cells restores expression of BiP and CHOP. H23-LKB1 and H23-KDLKB1 LA cells were treated with 20 mM 2DG for the indicated times (hours) and probed as in A. Actin and total AMPK were used as loading controls. Blot is representative of 4 independent experiments. (D) Reduction of LKB1 by siRNA knockdown attenuates UPR activation. LKB1 expressing H2009 or H358 were transfected with 100 nM siRNA targeting human LKB1 or a scrambled control and treated with 2DG (20 mM) 48 h after transfection for four hours. Lysates were immunoblotted with the indicated antibodies. Actin was used as a loading control. Blot is representative of 3 independent experiments.

The anti-tumorigenic properties of 2DG have been attributed to aggravation of existing ER stress in tumor cells via inhibition of glucose dependent protein glycosylation. Escalation of BiP is reflective of induction of ER stress, leading us to investigate the ER stress response in LKB1-deficient and LKB1-expressing NSCLC cells in response to 2DG. LKB1 expressing H2009 and LKB1-deficient H23 NSCLC cells were treated with 2DG and immunblotted for pAMPK and BiP/GRP78. Lysates were also immunoblotted for CHOP/GADD153 (C/EBP homologous protein/DDIT3), a protein whose expression is increased during both ER and metabolic stress. Treatment with 2DG (20 mM) resulted in phosphorylation of AMPK in LKB1 expressing H2009 cells, but not LKB1-deficient H23 cells (FIG. 3A) and apoptosis in H23 cells (supplemental FIG. 1A). In concordance with our in vivo staining (FIG. 2G-J), 2DG increased BiP in LKB1 expressing H2009 cells, while LKB1-deficient H23 cells displayed a more moderate increase (FIG. 3A). Protein levels of CHOP were also found to increase in LKB1 expressing H2009 cells upon treatment with 2DG, but not LKB1-deficient H23 (FIG. 3A). We expanded our analysis to additional LKB1 expressing (H358, H1975, H441) and LKB1-deficient (H2126, H838, H1395) NSCLC cell lines in order to determine if decreased CHOP and BiP expression in response to 2DG persisted in the absence of LKB1. LKB1-deficient H2126, H838 and H1395 NSCLC cells displayed minimal increases in CHOP and BiP with 2DG treatment after 12 h of treatment and increased apoptosis (cleaved PARP) after 18 h of treatment (FIG. 3B). The lack of LKB1 resulted in a failure to phosphorylate AMPK in response to 2DG (FIG. 3B). LKB1 expressing H358, H1975 and H441 cells displayed an opposite phenotype, with 2DG inducing AMPK phosphorylation and increasing CHOP and BiP protein levels (FIG. 3B). Stable expression of LKB1, but not a kinase-dead LKB1 (KDLKB1) in H23 NSCLC cells resulted in increases in BiP and CHOP protein expression, AMPK phosphorylation (FIG. 3C) and improved survival in response to 2DG treatment. To confirm the role of LKB1 in these observations, we depleted LKB1 in H2009 and H358 NSCLC cells using siRNA and assessed the effects of 2DG treatment. As shown in FIG. 3D, depletion of LKB1 in H2009 and H358 NSCLC cells resulted in reduced CHOP and BiP protein expressions (FIG. 3D), as well as reduced pAMPK (FIG. 3D) and reduced survival.

ER Stress Response is Altered in LKB1-Deficient NSCLC Cells

Figure 4:
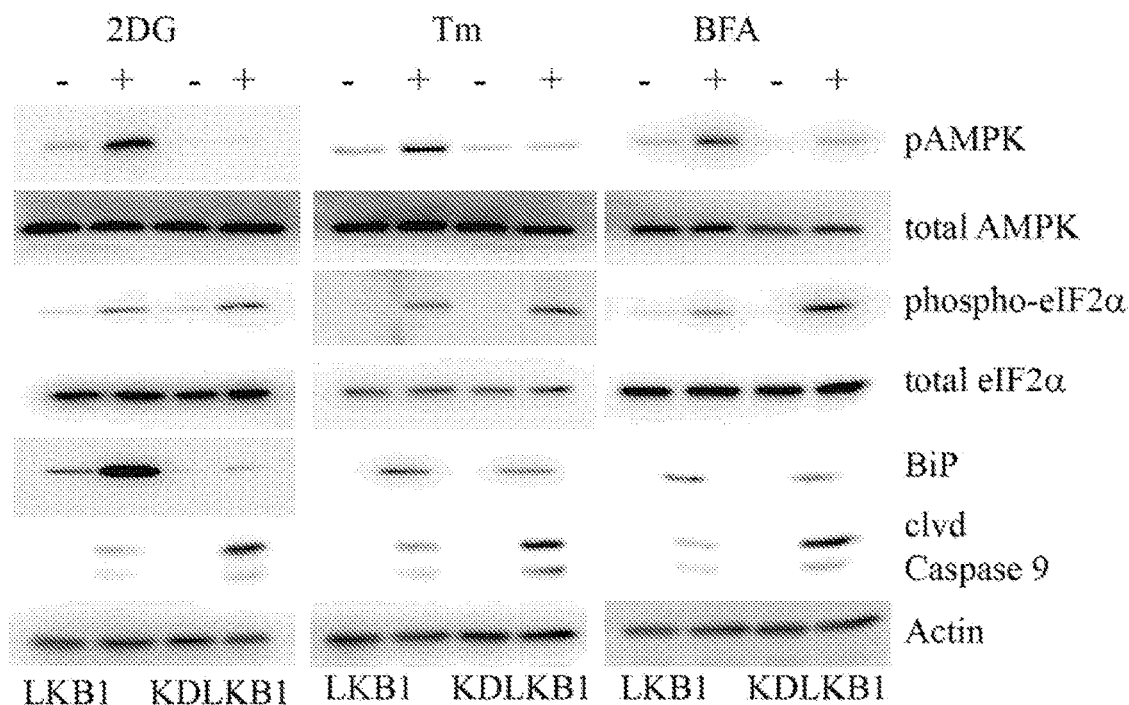
FIG. 4 depicts, in accordance with embodiments herein, response to ERSA treatment is altered in LKB1-deficient NSCLC cells. (A and B) H838 human NSCLC cells expressing full-length LKB1 (H838-LKB1) or kinase dead LKB1 (H838-KDLKB1) were treated with 2DG (10 mM), tunicamycin (Tm, 1.25 µg/ml) or brefeldin A (BFA, 30 ng/ml) for 12 (A) or 18 (B) hours. Lysates were immunoblotted with the indicated antibodies. Actin was used as loading controls. Blot is representative of 3 independent experiments.
Figure 4:
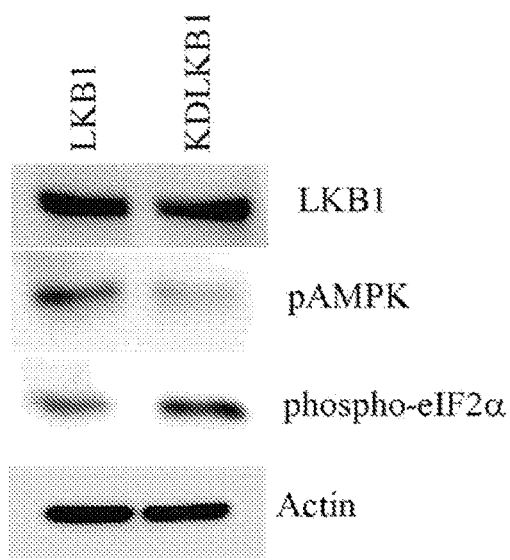

Although 2DG can induce ER stress, it also inhibits other glucose dependent processes, which could manifest itself in our observed phenotype in LKB1-deficient NSCLC cells. Thus we compared the effects of two pharmacological activators of ER stress (tunicamycin [Tm], brefeldin A [BFA]) to 2DG in derivatives of the LKB1-deficient NSCLC cell line, H838, stably expressing either wild-type LKB1 or kinase-dead LKB1 (KDLKB1). Protein levels of BiP increased in both H838-LKB1 and H838-KDLKB1 cells after 12 h of treatment with BFA (30 ng/ml) or Tm (1.25 ug/ml) (FIG. 4A). Interestingly, the relative difference in BiP levels between H838-LKB1 cells and H838-KDLKB1 were moderate compared to the effects upon BiP with 2DG (10 mM) treatment (FIG. 4A), perhaps related to 2DG inhibition of other glucose dependent functions. As such, we assessed the phosphorylation of the a subunit of the eukaryotic initiation factor 2 (eIF2/EIF2S1) that occurs in response to several stressors, including ER stress. Interestingly, H838-KDLKB1 cells displayed increased levels of phosphorylated eIF2a (phospho-eIF2a) following treatment with 2DG, Tm or BFA, compared to H838-LKB1 cells, contrary to the presence of reduced BiP (FIG. 4A).

Figure 5:
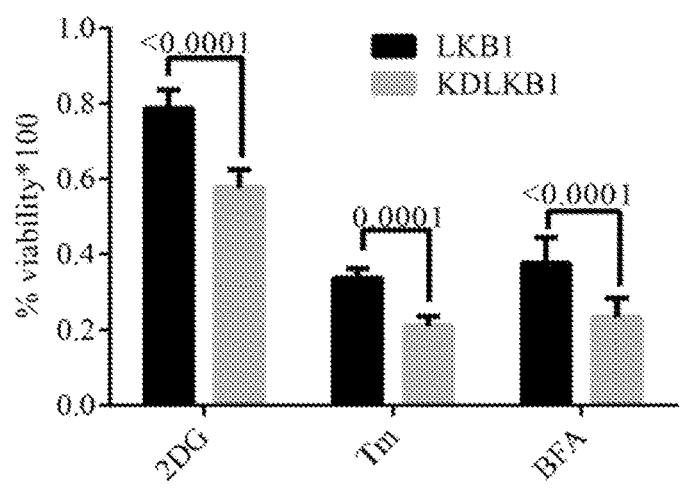
FIG. 5 shows, in accordance with embodiments herein, LKB1-deficient NSCLC cells are sensitive to ERSA treatment. (A and B) H838 (A) or A427 (B) LKB1-deficient human NSCLC cell lines expressing full-length LKB1 or kinase dead LKB1 (KDLKB1) were treated with 2DG (10 mM), Tm (1.25 µg/ml) or BFA (30 ng/ml) and ATP levels assessed by CellTiter Glo™. Levels of ATP were normalized to vehicle treated control. Graphs depict mean±SE from two independent experiments. (C) Clonogenic survival of H838-LKB1 and H838-KDLKB1 cells. H838 LKB1-deficient human NSCLC cell lines expressing full-length LKB1 or kinase dead LKB1 (KDLKB1) were treated with vehicle (DMSO), 2DG (10 mM), Tm (1.25 µg/ml) or BFA (30 ng/ml) with or without 125 ng/ml of cyclohexamide (CHX) for twenty-four hours. Surviving fraction was calculated as described in herein. Graph depicts mean±SE of three independent experiments.
Figure 5:
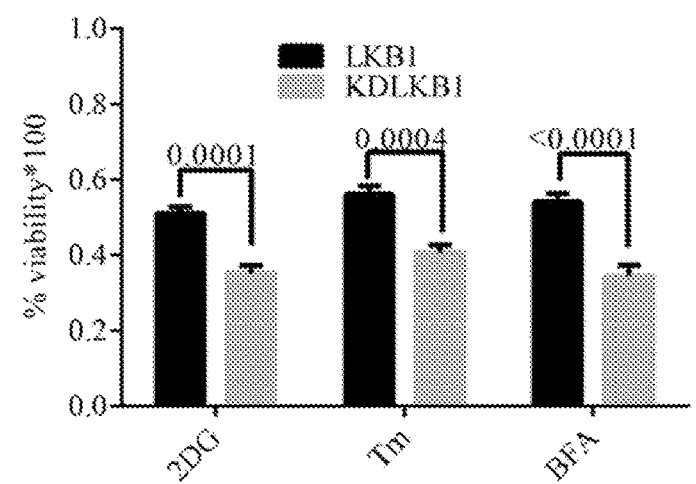
Figure 5:
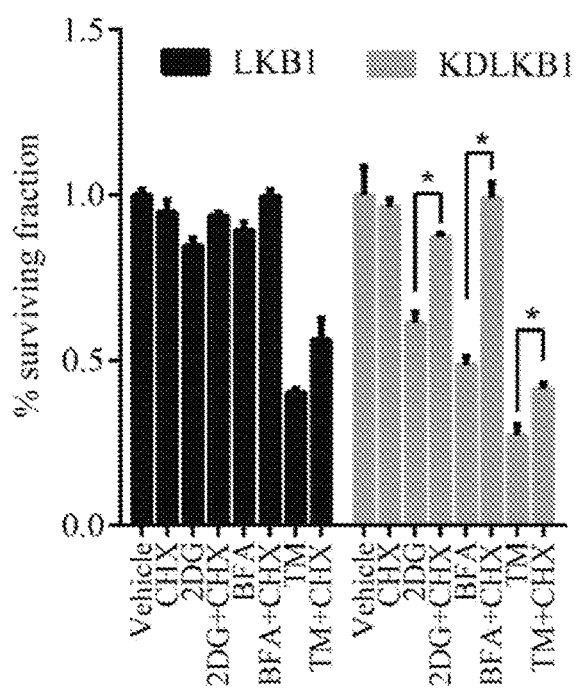

Activation of ER Stress in LKB1-Deficient NSCLC Results in UPR mediated Cell Death Under moderate levels of ER stress, functions of the UPR are protective, enabling adaptation and restoration of homeostasis within the cell. However in conditions of acute, irremediable ER stress, the UPR instead activates apoptosis. Increased phospho-eIF2a is found during acute, irremediable ER stress and is associated with ER stress induced cell death, leading us to assess whether 2DG, BFA and Tm were activating of UPR-mediated apoptosis in LKB1-deficient NSCLC cells. Expression of CHOP and activating transcription factor 4 (ATF4) function downstream of phosphor-eIF2a in initiation of UPR-mediated cell death. Analysis of protein lysates from H838-LKB1 and H838-KDLKB1 cells treated with 2DG, Tm or BFA for 18 h revealed increases in ATF4 (FIG. 4B) and equivalent levels of BiP for both cell lines (FIG. 4B). However, chronic treatment induced increased levels of CHOP in H838-KDLKB1, relative to H838-LKB1 cells (FIG. 4B). In addition, H838-KDLKB1 cells showed increased cleavage of caspase 9 (CASP9), a marker of ER stress-induced apoptosis, relative to H838-LKB1 after 18 h (FIG. 4B). Expression of ATF4 and CHOP have been linked to depletion of ATP, leading to cell death. Consistent with the hypothesis, treatment with 2DG, Tm or BFA all resulted in reduced ATP (FIG. 5B) in both H838-KDLKB1 (FIG. 5A) and A427-KDLKB1 (FIG. 5B), compared to H838 and A427 cells re-expressing LKB1 ($p<0.005$) and reduced cell survival of H838-KDLKB1 cells (FIG. 5C). As these effects of ATF4 and CHOP in UPR-mediated cell death are a result of reactivation of protein synthesis, we tested whether reducing protein load would ameliorate cytotoxicity of 2DG, BFA and Tm in the H838-KDLKB1 cell line. Cycloheximide (CHX) has been previously shown to reduce ER stress cytotoxicity by lowering the overall client proteins within the ER. The addition of CHX was able to ameliorate 2DG, BFA and Tm cytotoxicity in H838-KDLKB1 cells, compared to 2DG, BFA or Tm alone (FIG. 5C, $p<0.05$). ATF4 and CHOP activity leads to accumulation of reactive oxygen species (ROS), which contributes to cell death. Staining of ROS with CellROX™ in H838-LKB1 and H838-KDLKB1 cells showed that H838-KDLKB1 had markedly higher basal levels of ROS (1.4-fold increase in intensity over H838-LKB1), compared to H838-LKB1 cells (FIG. 6A-C, dotted lines mark baseline [blue peaks] ROS level of KDLKB1), consistent with recent reports of increased ROS in LKB1-deficient cells. ROS levels in H838-KDLKB1 increased further, relative to H838-LKB1, following treatment with 2DG (2-fold increase in intensity over H838-LKB1), BFA (1.2-fold increase in intensity over H838-LKB1) or Tm (1.67-fold increase in intensity over H838-LKB1) (FIG. 6A-C, red peak).

Although BFA and Tm function to induce ER stress within cells, neither is currently being explored for clinical use. Thus, we next tested bortezomib and celecoxib, which aggravates ER stress via a mechanism unrelated to COX-2 inhibition, for preferential cytotoxicity in LKB1-deficient cells. LKB1-deficient H23 NSCLC cells expressing KDLKB1 showed reduced expression of both BiP and CHOP following 18 h of exposure to either celecoxib (CHOP=1.3-fold decrease; BiP=1.6-fold decrease) or bortezomib (CHOP=1.6-fold decrease, BiP=9-fold decrease), compared to H23 cells with reconstituted LKB1; the presence of LKB1 correlated with phosphorylation of AMPK (FIG. 6D). In addition, both celecoxib and bortezomib reduced the survival of H23-KDLKB1 cells in a dose dependent manner, compared to H23-LKB1 NSCLC cells (FIG. 6E).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating non-small cell lung cancer (NSCLC) in a subject in need thereof, comprising:
   diagnosing a sensitivity to endoplasmic reticulum (ER) stress in the subject by assaying a sample of the subject to determine expression levels of C—C motif ligand 2 (CCL2) and Liver Kinase B1 (LKB1), wherein a higher expression level of CCL2 than a CCL2 reference level and a lower expression level of LKB1 than a LKB1 reference level indicates increased sensitivity to ER stress; and
   treating the subject by administering a therapeutically effective dosage of bortezomib.

2. The method of claim 1, wherein diagnosing sensitivity to ER stress further comprises detecting increases in phosphorylation of ER stress markers or detecting markers of ER stress mediated cell death.

3. The method of claim 2, wherein ER stress markers and markers of ER stress mediated cell death are selected from the group consisting of phosphorylated eukaryotic translation initiation factor 2 (eif2a), reactive oxygen species, cleaved caspase-9, cleaved poly(ADP-ribose) polymerase (PARP), phosphorylated inositol-requiring and endonuclease gene 1 (IRE1), 1 X-box binding protein-1 (XBP1) splicing, phosphorylated histone H2AX and combinations thereof.

4. The method of claim 1, wherein assaying the expression level of CCL2 comprises detecting an increase in transcription of CCL2.

5. The method of claim 1, further comprising treating the subject with one or more compounds selected from the group consisting of tunicamycin, brefeldin A, 2-deoxyglucose (2DG), celecoxib, nelfmavir, a heat shock protein 90 (HSP90) inhibitor, a heat shock protein 70 (HSP70) inhibitor, an autophagy inhibitor and combinations thereof.

6. The method of claim 5, wherein HSP90 inhibitor is geldanamycin, BEP800, or an analog thereof.

7. The method of claim 5, wherein the autophagy inhibitor is VER155008.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: synthetic contruct

<400> SEQUENCE: 1
tccttctggg tagacctctg ggag                                          24

<210> SEQ ID NO 2
<211> LENGTH: 24
<212> TYPE: DNA
<213> ORGANISM: Artificial Sequence
<220> FEATURE:
<223> OTHER INFORMATION: synthetic construct

<400> SEQUENCE: 2
aaacagagta gcagctcaga ctgc                                          24